United States Patent
Cheshire et al.

(10) Patent No.: US 6,469,014 B1
(45) Date of Patent: Oct. 22, 2002

(54) THIENO[2,3-D] PYRIMIDINEDIONES, THEIR PREPARATION AND USE IN THERAPY

(75) Inventors: David Cheshire, Loughborough; Andrew Cooke, Glasgow; Martin Cooper, Loughborough; David Donald, Loughborough; Mark Furber, Loughborough; Matthew Perry, Loughborough; Philip Thorne, Loughborough, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/977,944

(22) Filed: Oct. 17, 2001

Related U.S. Application Data

(63) Continuation of application No. 09/693,896, filed on Oct. 23, 2000, which is a continuation of application No. 09/117,426, filed on Jul. 30, 1998, now Pat. No. 6,180,635.

(30) Foreign Application Priority Data

May 28, 1997 (SE) ................................................ 9702001
May 18, 1998 (WO) ............................... PCT/SE98/00935

(51) Int. Cl.[7] ..................... C07D 495/04; A61K 31/505
(52) U.S. Cl. ..................................................... 514/260.1
(58) Field of Search ............................... 514/258, 260.1

(56) References Cited

FOREIGN PATENT DOCUMENTS

| EP | 0 640 606 A1 | 3/1995 |
| WO | 98/02162 | 1/1998 |

OTHER PUBLICATIONS

Serfling et al. The role of NFAT transcription factors in T cell activation and differentiation, Biochim. Biophys. Acta, 1498:1–18.*
Chemical Abstracts, vol. 112, pp. 722–723 (1990).
Gutschow et al, "3–Mercaptoalkylthieno[2,3–d]pyrimidin–2,4(1H,3H)–dione: Sythese . . . ," Arch. Pharm. (Weinheim), vol. 328, pp. 231–234 (1995).

* cited by examiner

*Primary Examiner*—Mukund J. Shah
*Assistant Examiner*—Hong Liu
(74) *Attorney, Agent, or Firm*—Nixon & Vanderhye

(57) ABSTRACT

The invention provides pharmaceutically useful thieno[2,3-d]pyrimidinediones, processes for their production, pharmaceutical compositions containing them and methods of treatment involving their use.

19 Claims, No Drawings

THIENO[2,3-D] PYRIMIDINEDIONES, THEIR PREPARATION AND USE IN THERAPY

This application is a continuation of application Ser. No. 09/693,896, filed Oct. 23, 2000, allowed, which is a continuation of application Ser. No. 09/117,426 filed Jul. 30, 1998, now U.S. Pat. No. 6,180,635, the entire content of which is hereby incorporated by reference in this application.

This invention relates to pharmaceutically useful compounds, processes for their production, pharmaceutical compositions containing them and methods of treatment involving their use.

T-cells play an important role in the immune response, however in autoimmune disease T-cells are activated against particular tissues, e.g. causing the inflammation associated with rheumatoid arthritis. Interleukin-2 (IL-2) is an essential autocrine growth factor for T-cells and hence inhibition of IL-2 transcription is beneficial in the modulation of autoimmune disease. Formation of a transcriptional complex of the protein nuclear factor of activated T-cells-1 (NFAT-1) on the IL-2 promoter is essential for IL2 transcription. NFAT-1 mediated transcription has therefore been proposed as appropriate molecular target for immunomodulation, Y. Baine et al., *J. Immunol.*, 1995, 154, 3667–3677.

W. F. Michne et al., in *J. Med. Chem.* (1995) 38, 2557–2569 disclose a number of quinazoline-2,4-diones and pyrrolo[3,4-d]pyrimidine-2,4-diones which inhibit transcription regulated by the DNA region bound by the NFAT-1 protein.

We have now found novel thieno[2,3-d] pyrimidinediones which exhibit pharmacological activity, in particular immunosuppressive activity.

In a first aspect the invention therefore provides a compound of formula (I):
wherein:

R is —C(O)Ar$^1$, —C(R$^4$)(R$^5$)Ar$^1$, or Ar$^2$;

Ar$^1$ is naphthyl, quinolyl, isoquinolyl, indolyl, benzofuranyl or benzothienyl, each of which can be optionally substituted by one or more substituents selected from $C_{1-4}$ alkyl, $C_{1-4}$ alkoxy, halogen or trifluoromethyl, or Ar$^1$ is phenyl optionally substituted by one or more substituents selected from $C_{1-4}$ alkyl, $C_{1-4}$ alkoxy, halogen, trifluoromethyl, amino, nitro, cyano, trifluoromethoxy, phenoxy, —CH$_2$N(R$^6$)$_2$, —NHSO$_2$CF$_3$, $C_{1-4}$alkylsulphonylamino, —NHC(O)R$^{6a}$, CO$_2$R$^7$ or —C(O)NR$^8$R$^{8a}$;

R$^4$ represents H or $C_{1-4}$ alkyl;

R$^5$ represents H or OH;

each R$^6$ independently represents H or $C_{1-4}$ alkyl, preferably methyl or ethyl;

R$^{6a}$ represents H, $C_{1-6}$ alkyl, aryl or ar$C_{1-4}$alkyl, wherein the aryl group or aryl moiety in the aralkyl group is phenyl or pyridyl, each of which may be optionally substituted by one or more substituents selected from $C_{1-4}$ alkyl, $C_{1-4}$ alkoxy, $C_{1-4}$ alkylcarbonylamino, halogen or trifluoromethyl;

R$^7$ represents H or $C_{1-4}$ alkyl, preferably methyl or ethyl;

R$^8$ and R$^{8a}$ each independently represent H, $C_{1-4}$ alkyl, preferably methyl or ethyl, phenyl or pyridyl;

Ar$^2$ is acenaphthenyl, indanyl, iminodihydrobenzofuranyl or fluorenyl, each of which can be optionally substituted by one or more substituents selected from OH, $C_{1-4}$ alkyl, $C_{1-4}$ alkoxy, halogen, or trifluoromethyl;

R$^1$ and R$^2$ are independently H, $C_{1-6}$ alkyl, $C_{3-6}$ alkenyl, CH$_2$C$_{3-5}$ cycloalkyl or $C_{3-6}$ cycloalkyl;

R$^3$ represents H, X—R$^9$ or X—Ar$^3$;

X represents S(O)$_n$, C(O)NR$^{10}$, C(O)O, NH(CO)NR$^{10}$, NH(CO)O or SO$_2$NR$^{10}$;

n is 0, 1 or 2;

R$^9$ represents a methyl group optionally substituted by one or more substituents selected from CN, CO$_2$H, $C_{1-5}$ alkoxycarbonyl, 5-tetrazolyl, SO$_2$NH$_2$, or C(O)NR$^{11}$R$^{12}$, or R$^9$ represents $C_{2-6}$ alkyl or $C_{3-6}$ alkenyl, each of which may be optionally substituted by one or more substituents selected from OH, CN, CO$_2$H, $C_{1-5}$ alkoxy, $C_{1-5}$ alkoxycarbonyl, 5-tetrazolyl, azide, phthalimido, SO$_2$NH$_2$, C(O)NR$^{11}$R$^{12}$, NR$^{13}$R$^{14}$, NHC(O)R$^{15}$ or NHSO$_2$R$^{16}$ where R$^{11}$, R$^{12}$, R$^{13}$ and R$^{14}$ each independently represent H or $C_{1-4}$ alkyl, R$^{15}$ represents $C_{1-4}$ alkyl, $C_{1-4}$ alkoxy, di($C_{1-4}$alkyl)amino, or alkoxyalkylene containing up to 6 carbon atoms, and R$^{16}$ represents $C_{1-4}$ alkyl or trifluoromethyl; or, additionally, in the case where X represents C(O)NR$^{10}$, NH(CO)NR$^{10}$ or SO$_2$NR$^{10}$, R$^9$ and R$^{10}$ together with the nitrogen atom to which they are attached may form a 4- to 7-membered heterocyclic ring which may be optionally substituted by one or more OH groups;

R$^{10}$ represents H, $C_{1-6}$ alkyl or is linked to R$^9$ as defined above; and Ar$^3$ is phenyl, pyridyl or pyridine N-oxide, each of which may be optionally substituted by one or more substituents selected from OH, NO$_2$, NH$_2$, NHSO$_2$CF$_3$, $C_{1-4}$ alkoxy, bis-$C_{1-4}$alkanesulphonylamino, $C_{1-4}$alkylcarbonylamino or $C_{1-4}$alkoxycarbonylamino;

or a pharmaceutically-acceptable salt or solvate thereof.

In the present specification, unless otherwise indicated, an alkyl or alkenyl group or an alkyl or alkenyl moiety in a substituent group may be linear or branched. Where a substituent in an alkenyl group is OH, phthalimido, NR$^{13}$R$^{14}$ or NHC(O)R$^{15}$, the substituent is not attached to an unsaturated carbon atom. The alkyl moieties in a di($C_{1-4}$ alkyl) amino group may be the same or different.

The group R is —C(O)Ar$^1$, —C(R$^4$)(R$^5$)Ar$^1$, or Ar$^2$.

The group R$^4$ represents H or $C_{1-4}$ alkyl, preferably methyl or ethyl, and the group R$^5$ represents H or OH.

Preferably Ar$^1$ is naphthyl, quinolyl, isoquinolyl, indolyl, benzofuranyl or benzothienyl, each of which can be optionally substituted by one to four, particularly one or two, substituents selected from $C_{1-4}$ alkyl (e.g. methyl or ethyl), $C_{1-4}$ alkoxy (e.g. methoxy or ethoxy), halogen (e.g. fluorine, chlorine or bromine) or trifluoromethyl, or Ar$^1$ is phenyl optionally substituted by one to four, particularly one or two, substituents selected from $C_{1-4}$ alkyl (e.g. methyl or ethyl), $C_{1-4}$ alkoxy (e.g. methoxy or ethoxy), halogen (e.g. fluorine, chlorine or bromine), trifluoromethyl, amino, nitro, cyano, trifluoromethoxy, phenoxy, —CH$_2$N(R$^6$)$_2$, —NHSO$_2$CF$_3$, $C_{1-4}$alkylsulphonylamino, —NHC(O)R$^{6a}$, CO$_2$R$^7$ or —C(O)NR$^8$R$^{8a}$.

Most preferably Ar$^1$ is naphthyl, quinolyl or benzofuranyl, or a phenyl group optionally substituted by one or two substituents selected from $C_{1-4}$ alkyl, $C_{1-4}$ alkoxy, halogen, trifluoromethyl, nitro, amino, cyano, phenoxy or —NHC(O)R$^{6a}$.

The group Ar$^2$ is preferably acenaphthenyl, indanyl, iminodihydrobenzofuranyl or fluorenyl, each of which can be optionally substituted by one to four, particularly one or two, substituents selected from OH, $C_{1-4}$ alkyl (e.g. methyl or ethyl), $C_{1-4}$ alkoxy (e.g. methoxy or ethoxy), halogen (e.g. fluorine, chlorine or bromine) or trifluoromethyl. Especially preferred are indanyl, iminodihydrobenzofuranyl and hydroxy-substituted indanyl groups.

$R^{6a}$ is preferably H, $C_{1-6}$, particularly $C_{1-4}$, alkyl, aryl or ar$C_{1-4}$alkyl, wherein the aryl group or aryl moiety in the aralkyl group is phenyl or pyridyl, each of which may be optionally substituted by one to four, especially one or two, substituents selected from $C_{1-4}$ alkyl (e.g. methyl or ethyl), $C_{1-4}$ alkoxy (e.g. methoxy or ethoxy), $C_{1-4}$ alkylcarbonylamino (e.g. methyl- or ethylcarbonylamino), halogen (e.g. fluorine, chlorine or bromine) or trifluoromethyl.

Most preferably, $R^{6a}$ represents a phenyl or phenyl$C_{1-4}$alkyl group substituted in the aromatic ring by one or two substituents selected from methoxy and methylcarbonylamino.

Preferably $R^1$ and $R^2$ are independently H, $C_{1-4}$ alkyl, $C_{3-4}$ alkenyl or $C_{3-6}$ cycloalkyl.

It is preferred that $R^1$ is $C_{3-4}$ alkyl or $C_4$ alkenyl, in particular 1-methylethyl, 2-methylpropyl or 2-methylpropenyl.

It is preferred that $R^2$ is H or, especially, methyl.

$R^3$ represents H, X—$R^9$ or X—$Ar^3$.

X represents $S(O)_n$ where n is 0, 1 or 2, $C(O)NR^{10}$, $C(O)O$, $NH(CO)NR^{10}$, $NH(CO)O$ or $SO_2NR^{10}$.

Preferably $R^9$ represents a methyl group optionally substituted by CN, $CO_2H$, $C_{1-5}$ alkoxycarbonyl, 5-tetrazolyl, $SO_2NH_2$ or $C(O)NR^{11}R^{12}$, or $R^9$ preferably represents $C_{2-6}$ alkyl or $C_{3-6}$ alkenyl, each of which may be optionally substituted by one to four, particularly one or two, substituents selected from OH, CN, $CO_2H$, $C_{1-5}$ alkoxy, $C_{1-5}$ alkoxycarbonyl, 5-tetrazolyl, azide, phthalimido, $SO_2NH_2$, $C(O)NR^{11}R^{12}$, $NR^{13}R^{14}$, $NHC(O)R^{15}$ or $NHSO_2R^{16}$ where $R^{11}$, $R^{12}$, $R^{13}$ and $R^{14}$ each independently represent H or $C_{1-4}$ alkyl, particularly methyl or ethyl, $R^{15}$ represents $C_{1-4}$ alkyl, particularly methyl or ethyl, $C_{1-4}$ alkoxy, particularly methoxy or ethoxy, di($C_{1-4}$alkyl)amino, particularly dimethylamino or diethylamino, or alkoxyalkylene containing from 2 to 4 carbon atoms, and $R^{16}$ represents $C_{1-4}$ alkyl, preferably methyl or ethyl, or trifluoromethyl; or, additionally, in the case where X represents $C(O)NR^{10}$, $NH(CO)NR^{10}$ or $SO_2NR^{10}$, $R^9$ and $R^{10}$ together with the nitrogen atom to which they are attached may form a 5- or 6-membered heterocyclic ring which may be optionally substituted by one or two OH groups.

More preferably $R^9$ represents a methyl group optionally substituted by $CO_2H$ or $C(O)NR^{11}R^{12}$, or a $C_{2-4}$ alkyl group (e.g. ethyl, propyl or butyl) which may be optionally substituted by one or two substituents selected from OH, $CO_2H$, $C_{1-5}$ alkoxycarbonyl (e.g. methoxycarbonyl or ethoxycarbonyl), azide, phthalimido, $NR^{13}R^{14}$, $NHC(O)R^{15}$ or $NHSO_2R^{16}$; or $R^9$ and $R^{10}$ together with the nitrogen atom to which they are attached form a 5- or 6-membered heterocyclic ring which may be optionally substituted by an OH group.

Preferably, $R^{10}$ represents H, $C_{1-2}$ alkyl, especially methyl, or is linked to $R^9$ as defined above.

Most preferably, each of $R^{11}$, $R^{12}$, $R^{13}$ and $R^{14}$ represents hydrogen.

Most preferably, $R^{15}$ represents methyl, methoxy, dimethylamino or methoxymethylene.

Most preferably, $R^{16}$ represents methyl or trifluoromethyl.

Preferably, $Ar^3$ is phenyl, pyridyl or pyridine N-oxide, each of which may be optionally substituted by one to four, particularly one or two, substituents selected from OH, $NO_2$, $NH_2$, $NHSO_2CF_3$, $C_{1-4}$ alkoxy (particularly methoxy or ethoxy), bis-$C_{1-4}$alkanesulphonylamino (particularly bis-$C_{1-2}$alkanesulphonylamino), $C_{1-4}$alkylcarbonylamino (particularly $C_{1-2}$alkylcarbonylamino) or $C_{1-4}$alkoxycarbonylamino (particularly $C_{1-2}$alkoxycarbonylamino).

The group $Ar^3$ is very preferably phenyl, pyridyl or pyridine N-oxide, each of which may be optionally substituted by one or two substituents selected from OH, $NO_2$, $NH_2$, methoxy, bis-methanesulphonylamino, methylcarbonylamino or methoxycarbonylamino.

Particularly preferred compounds of the invention include:

6-(4-Methoxyphenylmethyl)-3-methylthieno[2,3-d]pyrimidine-2,4(1H,3H)-dione, 6-(4-Methoxyphenylmethyl)-3-methyl-1-(2-methyl-2-propenyl)thieno[2,3-d]pyrimidine-2,4(1H,3H)-dione, 1-(2-Methylpropyl)-6-(1-naphthalenylmethyl)thieno[2,3-d]pyrimidine-2,4(1H,3H)-dione, 3-Methyl-1-(2-methylpropyl)-6-(1-naphthalenylmethyl)thieno[2,3-d]pyrimidine-2,4(1H,3H)-dione, 3-Methyl-1-(2-methylpropyl)-6-(1-naphthalenylmethyl)-5-[(2-pyridinyl)thio]thieno[2,3-d]pyrimidine-2,4(1H,3H)-dione, 5-[(3-Hydroxypropyl)thio]-3-methyl-1-(2-methylpropyl)-6-(1-naphthalenylmethyl)thieno[2,3-d]pyrimidine-2,4(1H,3H)-dione, Methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate, 4-[(1,2,3,4-Tetrahydro-3-methyl-1-(2-methylpropyl)-6-(1-naphthalenylmethyl)-2,4-dioxothieno[2,3-d]pyrimidin-5-yl)thio]butanoic acid, Methyl 4-[(1,2,3,4-tetrahydro-3-methyl-1-(2-methylpropyl)-6-(1-naphthalenylmethyl)-2,4-dioxothieno[2,3-d]pyrimidin-5-yl)sulfinyl]butanoate, Methyl 4-[(1,2,3,4-tetrahydro-3-methyl-1-(2-methylpropyl)-6-(1-naphthalenylmethyl)-2,4-dioxothieno[2,3-d]pyrimidin-5-yl)sulfonyl]butanoate, 4-[(1,2,3,4-Tetrahydro-3-methyl-1-(2-methylpropyl)-6-(1-naphthalenylmethyl)-2,4-dioxothieno[2,3-d]pyrimidin-5-yl)sulfonyl]butanoic acid, 6-Benzyl-3-methyl-1-(2-methylpropyl)thieno[2,3-d]pyrimidine-2,4(1H,3H)-dione, 3-Methyl-1-(1-methylethyl)-6-(phenylmethyl)thieno[2,3-d]pyrimidine-2,4(1H,3H)-dione, 6-[(1-Hydroxy-1-phenyl)methyl]-3-methyl-1-(2-methylpropyl)thieno[2,3-d]-pyrimidine-2,4(1H,3H)-dione, (±) 5-[(2-Hydroxypropyl)thio]-3-methyl-1-(2-methylpropyl)-6-(1-naphthalenylmethyl)thieno[2,3-d]pyrimidine-2,4(1H,3H)-dione, 1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-carboxamide, (3R)-1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}pyrrolidin-3-ol, 1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}piperidin-4-ol, (3R)-1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}piperidin-3-ol, 1,2,3,4-Tetrahydro-N-(2-hydroxyethyl)-3,N-dimethyl-1-(2-methylpropyl)-6-(1-naphthalenylmethyl)-2,4-dioxothieno[2,3-d]pyrimidine-5-carboxamide, 2-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}acetic acid, 3-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}propanoic acid, 2-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}acetamide, 1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}pyrrolidine, 1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-sulfonamide, 5-[(3-Methoxyphenyl)thio]-3-methyl-1-(2-methylpropyl)-6-(1-naphthalenylmethyl)thieno[2,3-d]pyrimidine-2,4-(1H,3H)-dione, 5-[(3-Hydroxyphenyl)thio]-3-methyl-1-(2-methylpropyl)-6-(1-naphthalenylmethyl)thieno[2,3-d]pyrimidine-2,4-(1H,3H)-dione, 5-[(3-Hydroxyphenyl)sulfinyl]-3-methyl-1-(2-methylpropyl)-6-(1-naphthalenylmethyl)thieno[2,3-d]pyrimidine-2,4-(1H,3H)-dione, 5-[(3-Hydroxyphenyl)sulfonyl]-3-methyl-1-(2-methylpropyl)-6-(1-naphthalenylmethyl)thieno[2,3-d]pyrimidine-2,4-(1H,3H)-dione, 3-Methyl-1-(2-methylpropyl)-6-(1-naphthalenylmethyl)-5-[(3-nitophenyl)thio]thieno[2,3-d]pyrimidine-2,4-(1H,3H)-dione, 5-[(3-Aminophenyl)thio]-3-methyl-1-(2-methylpropyl)-6-(1-naphthalenylmethyl)thieno[2,3-d]pyrimidine-2,4-(1H,3H)-dione, 5-{[3-{(Bis-methanesulfonyl)amino}phenyl]thio-3-methyl-2-(2-methylpropyl)-6-(1-naphthalenylmethyl)thieno[2,3-d]pyrimidine-2,4-(1H,3H)-dione, 5-[(3-Methoxycarbonylaminophenyl)thio]-3-methyl-1-(2-methylpropyl)-6-(1-naphthalenylmethyl)thieno[2,3-d]pyrimidine-2,4-(1H,3H)-dione, 5-[(3-Acetamidophenyl)thio]-3-methyl-1-(2-methylpropyl)-6-(1-naphthalenylmethyl)thieno[2,3-d]pyrimidine-2,4-(1H,3H)-dione, 3-Methyl-1-(2-methylpropyl)-6-(1-naphthalenylmethyl)-5-[(4-nitrophenyl)thio]thieno[2,3-d]pyrimidine-2,4-(1H,3H)-dione, 5-[(4-Aminophenyl)thio]-3-methyl-1-(2-methylpropyl)-6-(1-naphthalenylmethyl)thieno[2,3-d]pyrimidine-2,4-(1H,3H)-dione, 3-Methyl-1-(2-methylpropyl)-6-(1-naphthalenylmethyl)-5-[(5-nitropyridin-2-yl)thio]thieno[2,3-d]pyrimidine-2,4-(1H,3H)-dione, 2-{[1,2,3,4-Tetrahydro-3-methyl-1-(2-methylpropyl)-6-(1-naphthalenylmethyl)-2,4-dioxothieno[2,3-d]pyrimidin-5-yl]thio}pyridine N-oxide, 5-[(3-Azidopropyl)thio]-3-methyl-1-(2-methylpropyl)-6-(1-naphthalenylmethyl)thieno[2,3-d]pyrimidine-2,4(1H,3H)-dione, 5-[(3-Aminopropyl)thio]-3-methyl-1-(2-methylpropyl)-6-(1-naphthalenylmethyl)thieno[2,3-d]pyrimidine-2,4(1H,3H)-dione, N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}acetamide, N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-N',N'-dimethylurea, N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-methoxyacetamide, Methyl N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}carbamate, N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}methanesulfonamide, N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}trifluoromethanesulfonamide, 5-{[3-(1,3-Dihydro-1,3-dioxo-2H-isoindol-2-yl)propyl]thio}-3-methyl-1-2-methylpropyl)-6-(1-naphthalenylmethyl)thieno[2,3-d]pyrimidine-2,4(1H,3H)-dione, N-(2-Hydroxyethyl)-N'-[1,2,3,4-tetrahydro-3-methyl-1-(2-methylpropyl)-6-(1-naphthalenylmethyl)-2,4-dioxothieno[2,3-d]pyrdin-5-yl)]urea, 2-Hydroxyethyl[1,2,3,4-tetrahydro-3-methyl-1-(2-methylpropyl)-6-(1-naphthalenylmethyl)-2,4-dioxothieno[2,3-d]pyrimidin-5-yl]carbamate, N-(2-Hydroxyethyl)-N-methyl-N'-[1,2,3,4-tetrahydro-3-methyl-1-(2-methylpropyl)-6-(1-naphthalenylmethyl)-2,4-dioxothieno[2,3-d]pyrimidin-5-yl)]urea, 6-[(1-Hydroxy-1-(3-fluorophenyl))methyl]-3-methyl-1-(2-methylpropyl)thieno[2,3-d]pyrimidine-2,4-(1H,3H)-dione, 6-[(3-Fluorophenyl)methyl]-3-methyl-1-(2-methylpropyl)thieno[2,3-d]pyrimidine-2,4-(1H,3H)-dione, 6-[(1-Hydroxy-1-(2-bromophenyl))methyl]-3-methyl-1-(2-methylpropyl)thieno[2,3-d]pyrimidine-2,4(1H,3H)-dione, 6-[(1-Hydroxy-1-(2-methylphenyl))methyl]-3-methyl-1-(2-methylpropyl)thieno[2,3-d]pyrimidine-2,4(1H,3H)-dione, 6-[(1-Hydroxy-1-(3-cyanophenyl))methyl]-3-methyl-1-(2-methylpropyl)thieno[2,3-d]pyrimidine-2,4(1H,3H)-dione, 6-[(1-Hydroxy-1-(3-trifluoromethylphenyl))methyl]-3-methyl-1-(2-methylpropyl)thieno[2,3-d]pyrimidine-2,4(1H,3H)-dione, 6-[(1-Hydroxy-1-(3-phenyloxyphenyl))methyl]-3-methyl-1-(2-methylpropyl)thieno-[2,3-d]pyrimidine-2,4(1H,3H)-dione, 6-[(1-Hydroxy-1-(1-naphthalenyl))methyl]-3-methyl-1-(2-methylpropyl)thieno[2,3-d]pyrimidine-2,4(1H,3H)-dione, 6-[(1-Hydroxy-1-(6-quinolinyl))methyl]-3-methyl-1-(2-methylpropyl)thieno[2,3-d]pyrimidine-2,4(1H,3H)-dione, 6-[(1-Hydroxy-1-(4-quinolinyl))methyl]-3-methyl-1-(2-methylpropyl)thieno[2,3-d]pyrimidine-2,4(1H,3H)-dione, (±) 6-[1-(Benzo[b]furan-2-yl)-1-hydroxymethyl]-3-methyl-1-(2-methylpropyl))thieno[2,3-d]pyrimidine-2,4(1H,3H)-dione, 6-[(1-Hydroxy-1-(2-chloro-6-fluorophenyl))methyl]-3-methyl-1-(2-methylpropyl)thieno-[2,3-d]pyrimidine-2,4(1H,3H)-dione, 6-[(1-Hydroxy-1-phenyl)ethyl]-3-methyl-1-(2-methylpropyl)thieno[2,3-d]pyrimidine-2,4(1H,3H)-dione, 6-[(1-Hydroxy-1-(4-trifluoromethylphenyl))methyl]-3-methyl-1-(2-methylpropyl)thieno[2,3-d]pyrimidine-2,4(1H,3H)-dione, (±) 6-(2,3-dihydro-1-hydroxy-1H-indenyl)-3-methyl-1-(2-methylpropyl)thieno[2,3-d]pyrimidine-2,4(1H,3H)-dione, 6-[(1-Hydroxy-1-(2-quinolinyl))methyl]-3-methyl-1-(2-methylpropyl)thieno[2,3-d]pyrimidine-2,4(1H,3H)-dione, 6-(1-Hydroxy-1-[3-quinolinyl]methyl)-3-methyl-1-(2-methylpropyl)thieno[2,3-d]pyrimidine-2,4(1H,3H)-dione, 6-(2-bromophenylmethyl)-3-methyl-1-(2-methylpropyl)thieno[2,3-d]pyrimidine-2,4(1H,3H)-dione, 6-(2-methylphenylmethyl)-3-methyl-1-(2-methylpropyl)thieno[2,3-d]pyrimidine-2,4(1H,3H)-dione, 6-(3-cyanophenylmethyl)-3-methyl-1-(2-methylpropyl)thieno[2,3-d]pyrimidine-2,4(1H,3H)-dione, 6-(3-trifluoromethylphenylmethyl)-3-methyl-1-(2-methylpropyl)thieno[2,3-d]pyrimidine-2,4(1H,3H)-dione, 6-(3-phenyloxyphenylmethyl)-3-methyl-1-(2-methylpropyl)thieno[2,3-d]pyrimidine-2,4(1H,3H)-dione, 3-Methyl-1-(2-methylpropyl)-6-(4-quinolinylmethyl)thieno[2,3-d]pyrimidine-2,4(1H,3H)-dione, 3-Methyl-1-(2-methylpropyl)-6-(6-quinolinylmethyl)thieno[2,3-d]pyrimidine-2,4(1H,3H)-dione, 3-Methyl-1-(2-methylpropyl)-6-(2-quinolinylmethyl)thieno[2,3-d]pyrimidine-2,4(1H,3H)-dione, trifluoroacetic acid salt, 6-(2-Benzo[b]furanylmethyl)-3-methyl-1-(2-methylpropyl)-)thieno[2,3-d]pyrimidine-2,4(1H,3H)-dione, 6-(2-Chloro-6-fluorophenylmethyl)-3-methyl-1-(2-methylpropyl)thieno[2,3-d]pyrimidine-2,4(1H,3H)-dione, 6-(1-Phenylethyl)-3-methyl-1-(2-methylpropyl)thieno[2,3-d]pyrimidine-2,4(1H,3H)-dione 6-(4-Trifluoromethylphenylmethyl)-3-methyl-1-(2-methylpropyl)thieno[2,3-d]pyrimidine-2,4(1H,3H)-dione, (±) 6-(2,3-dihydro-1H-inden-1-yl)-3-methyl-1-(2-methylpropyl)thieno[2,3-d]pyrimidine-2,4(1H,3H)-dione, 6-(3-Imino-1,3-dihydro-benzo[c]furan-1-yl)-3-methyl-1-(2-methylpropyl)thieno[2,3-d]pyrimidine-2,4(1H,3H)-dione, 2-[(1,2,3,4-tetrahydro-3-methyl-1-(2-methylpropyl)-2,4-dioxothieno[2,3-d]pyrimidin-6-yl)methyl]benzamide, (±) 6-(1-Hydroxy-1-[1-naphthalenyl]methyl)-5-([3-hydroxypropyl]thio)-3-methyl-1-(2-methylpropyl)thieno[2,3-d]pyrimidine-2,4(1H,3H)-dione, 3-Methyl-1-(2-methylpropyl)-6-(1-naphthalenylcarbonyl)thieno[2,3-d]pyrimidine-2,4(1H,3H)-dione, (±)-5-[(3-Hydroxybutyl)thio]-3-methyl-1-(2-methylpropyl)-6-(1-naphthalenylmethyl)thieno[2,3-d]pyrimidine-2,4(1H,3H)-dione, 6-(3-Fluorophenyl)methyl-5-[(3-hydroxypropyl)thio]-3-methyl-1-(2-methylpropyl)thieno[2,3-d]pyrimidine-2,4(1H,3H)-dione, 5-[(5-Amino-2-pyridinyl)thio]-3-methyl-1-(2-methylpropyl)-6-(1-naphthalenylmethyl)thieno[2,3-d]pyrimidine-2,4(1H,3H)-dione, Ethyl 1,2,3,4-tetrahydro-3-methyl-1-(2-methylpropyl)-6-phenylmethyl-2,4-dioxothieno[2,3-d]pyrimidine-5-carboxylate, 1,2,3,4-Tetrahydro-3,N,N-trimethyl-1-(2-methylpropyl)-6-phenylmethyl-2,4-dioxothieno[2,3-d]pyrimidine-5-carboxamide, 6-[1-Hydroxy-(4-nitrophenyl)methyl-3-methyl-1-(2-methylpropyl)thieno[2,3-d]pyrimidin-2,4(1H,3H)-dione, 6-(4-Nitrophenylmethyl)-3-methyl-1-(2-methylpropyl)thieno[2,3-d]pyrimidin-2,4(1H,3H)-dione, 6-(4-Aminophenylmethyl)-3-methyl-1-(2-methylpropyl)thieno[2,3-d]pyrimidine-2,4-(1H,3H)-dione, 4-(3,4-Dimethoxyphenyl)-N-{4-[(1,2,3,4-tetrahydro-3-methyl-1-(2-methylpropyl)-2,4-dioxothieno[2,3-d]pyrimidin-6-yl)methyl]phenyl}-butanamide, and 3-Acetamido-N-(4-[1,2,3,4-tetrahydro-3-methyl-1-(2-methylpropyl)-2,4-dioxothieno[2,3-d]pyrimidin-6-yl)methyl]phenyl)benzamide.

According to the invention there is also provided a process for the preparation of a compound of formula (I) which comprises:

(a) preparation of a compound of formula (I) wherein X is $SO_2$, by oxidation of a compound of formula (I) wherein X is $S(O)_n$ and n is 0 or 1, in the presence of an appropriate oxidising agent (e.g. 3-chloroperoxybenzoic acid) and an appropriate solvent (e.g. dichloromethane) for example at 0° C. to ambient temperature (20° C.); or (b) preparation of a compound of formula (I) wherein X is SO, by oxidation of a compound of formula (I) wherein X is S, in the presence of an appropriate quantity of a suitable oxidising agent (e.g. potassium peroxymonosulphate, commercially sold under the trade mark "OXONE") in a suitable solvent (e.g. aqueous methanol), for example, at ambient temperature; or (c) preparation of a compound of a formula (I) wherein X is S, by reacting a compound of general formula
wherein R, $R^1$ and $R^2$ are as hereinbefore defined, with a compound of general formula (III), $R^{17}$—S—S—$R^{17}$, wherein the groups $R^{17}$ both represent $R^9$ or $Ar^3$ as previously defined, or with a compound of general formula (IV), L—S—$R^{17}$, wherein L represents a leaving group such as an arylsulphinate group and $R^{17}$ is as defined above, in the presence of lithium diisopropylamide at a temperature from −78° C. to 50° C.; or (d) preparation of a compound of formula (I) wherein $R^3$ represents H, by reaction of a compound of general formula
wherein $R^{18}$ and $R^{19}$ each independently represent an alkyl (e.g. ethyl) or aryl group and R and $R^1$ are as hereinbefore defined, with a compound of general formula (VI), $R^2NH_2$, wherein $R^2$ is as hereinbefore defined, in the presence of a suitable solvent (e.g. ethanol), for example, at elevated temperature and pressure; or (e) preparation of a compound of formula (I) wherein X is $C(O)NR^{10}$, by reacting a compound of general formula
wherein R, $R^1$ and $R^2$ are as hereinbefore defined, with a compound of general formula
wherein $R^9$ and $R^{10}$ are as hereinbefore defined, in the presence of 1-(3-dimethylaminopropyl)-3-ethylcarbodiimide and 1-hydroxybenzotriazole hydrate;

(f) preparation of a compound of formula (I) wherein X is $NH(CO)NR^{10}$, by reacting a compound of general formula
wherein R, $R^1$ and $R^2$ are as hereinbefore defined, with a compound of formula (VIII) as described above, in the presence of a solvent such as toluene; or (g) preparation of a compound of formula (I) wherein X is NH(CO)O, by reacting a compound of formula (IX) as defined above, with a compound of general formula (X), $R^9OH$, wherein $R^9$ is as hereinbefore defined, in the presence of a solvent such as toluene; or (h) preparation of a compound of formula (I) wherein X is $SO_2NR^{10}$, by reacting a compound of general formula
wherein $L^1$ represents a leaving group such as a halogen atom (e.g. chlorine) and R, $R^1$ and $R^2$ are as hereinbefore defined, with a compound of formula (VIII) as defined above, in the presence of a solvent such as dichloromethane; or (i) preparation of a compound of formula (I) wherein X is C(O)O, by reacting a compound of general formula wherein $R^{3'}$ represents $CO_2R^9$ or $CO_2Ar^3$ and R, $R^1$, $R^{18}$ and $R^{19}$ are as hereinbefore defined, with a compound of general formula (VI) as hereinbefore defined, in the presence of a suitable solvent (e.g. ethanol), for example, at elevated temperature and pressure;

and optionally after (a), (b), (c), (d), (e), (f), (g), (h) or (i) converting the compound of formula (I) obtained to a further compound of formula (I) and/or forming a pharmaceutically-acceptable salt or solvate thereof.

Compounds of formula (II) in which R is —C(=O)$Ar^1$ may conveniently be prepared by reacting a compound of general formula
in which $R^1$ and $R^2$ are as hereinbefore defined, with a compound of general formula (XIII), $Ar^1COCl$, in the presence of aluminium (III) chloride and a solvent such as 1,2-dichloroethane under reflux conditions; or, alternatively, by oxidising a compound of general formula
in which $R^4$ represents H, $R^5$ represents OH and $R^1$ and $R^2$ are as previously defined, in the presence of potassium permanganate and 1,4,7,10,13,16-hexaoxacyclooctadecane (commercially sold as "18-Crown-6") in a solvent such as dichloromethane at ambient temperature.

Compounds of formula (XIV) in which $R^5$ is OH and $R^1$, $R^2$, $R^4$ and $Ar^1$ are as hereinbefore defined may be prepared by reacting a compound of formula (XII) as defined above with a compound of general formula
in which $R^4$ is as hereinbefore defined in the presence of lithium diisopropylamide at a temperature from −78° C. to 50° C.

Compounds of formula (XIV) in which $R^5$ is H and $R^1$, $R^2$, $R^4$ and $Ar^1$ are as hereinbefore defined may be readily prepared by reducing a corresponding compound of formula (XIV) in which $R^5$ is OH in the presence of triethylsilane and trifluoroacetic acid at ambient temperature.

Compounds of formula (II) in which R is $Ar^2$ can be prepared by reacting a compound of formula (XII) as hereinbefore defined with 1-indanone, 2-indanone, 9-fluoreneone or 1-acenapthenone in the presence of lithium diisopropylamide and optionally cerium (III) chloride at −78° C. to 50° C. temperature, followed by a reduction reaction, e.g. in the presence of triethylsilane and trifluoroacetic acid.

Compounds of formula (V) may conveniently be prepared by reacting a compound of general formula
to wherein R, $R^1$ and $R^{18}$ are as hereinbefore defined, with a compound of general formula
wherein $R^{19}$ is as hereinbefore defined and Hal is a halogen atom (e.g. chlorine), in the presence of a suitable base (e.g. triethylamine) and a solvent such as dichloromethane.

Compounds of formula (XVI) in which $R^1$ is H may be prepared by reacting a compound of general formula (XVIII), R—$CH_2CHO$, wherein R is as previously defined, with a compound of general formula
wherein $R^{18}$ is as previously defined, and with elemental sulfur, in a suitable solvent, e.g. dimethylformamide.

Compounds of formula (XVI) in which $R^1$ is $CH_2C_{1-5}$ alkyl, $CH_2C_{2-5}$ alkenyl or $CH_2C_{3-5}$cycloalkyl may suitably be prepared by reacting a corresponding compound of formula (XVI) in which $R^1$ is H, with a compound of general formula (XX), $R^{20}CO_2H$, wherein $R^{20}$ represents $C_{1-5}$ alkyl, $C_{2-5}$ alkenyl or $C_{3-5}$ cycloalkyl, and with a reducing agent such as sodium borohydride, in the absence of a solvent.

Compounds of formula (XVI) in which $R^1$ is $C_{1-6}$ alkyl or $C_{3-6}$ cycloalkyl may conveniently be prepared by reacting a corresponding compound of formula (XVI) in which $R^1$ is H, in the presence of a solvent such as toluene and catalytic toluenesulphonic acid under reflux conditions, with a compound of general formula
wherein the groups $R^{21}$ are both methyl or ethyl groups, and $R^{22}$ and $R^{23}$ each independently represent a hydrogen atom or an alkyl group or together form a hydrocarbyl ring, the total number of carbon atoms in $R^{22}$ and $R^{23}$ taken together not exceeding five, followed by reaction with a reducing agent such as sodium borohydride.

Compounds of formula (Va) may be prepared in a similar manner to the compounds of formula (V) but using in place of the compound of formula (XVI), a compound of general formula
in which R, $R^1$, $R^{3'}$ and $R^{18}$ are as previously defined.

Compounds of formula (XXII) in which $R^1$ is H may be prepared by reacting a compound of general formula (XXIII), $RCH_2C(O)R^{3'}$, wherein R and $R^{3'}$ are as previously defined, with a compound of formula (XIX) as hereinbefore defined and also with elemental sulfur in a suitable solvent.

Compounds of formula (XXII) in which $R^1$ is other than hydrogen may be prepared by processes analogous to those described above for the preparation of compounds of formula (XVI) in which $R^1$ is other than hydrogen.

Compounds of formula (VII) may suitably be prepared by reacting a compound of formula (II) above with carbon dioxide in the presence of lithium diisopropylamide, e.g. in tetrahydrofuran at a temperature from −78° C. to 50° C. under pressure.

Compounds of formula (IX) may be easily prepared by reacting a compound of formula (VII) as described above with diphenylphosphoryl azide, $(C_6H_5O)_2P(O)N_3$, in the presence of a solvent, e.g. a mixture of triethylamine and toluene.

Compounds of formula (XI) in which $L^1$ represents a halogen atom such as chlorine can be prepared by reacting a compound of formula (II) as defined above with lithium diisopropylamide and sulfur dioxide to form an intermediate which is then further reacted with N-chlorosuccinimide and aqueous hydrochloric acid, in the presence of a solvent such as dichloromethane.

Compounds of formula (I) can be converted into further compounds of formula (I) using standard procedures. For example, compounds of formula (I) where $Ar^3$ is nitrophenyl can be converted to compounds of formula (I) where $Ar^3$ is aminophenyl by reduction using iron powder and ammonium chloride in ethanol under reflux conditions; or compounds of formula (I) where $Ar^3$ is pyridyl can be converted to compounds of formula (I) where $Ar^3$ is pyridine N-oxide by reaction with 3-chloroperoxybenzoic acid in a solvent such as dichloromethane.

Compounds of formula (III), (IV), (VI), (VIII), (X), (XII), (XIII), (XV), (XVII), (XVIII), (XIX), (XX), (XXI) and (XXIII) are either commercially available, are well known in the literature or may be prepared easily using known techniques.

It will be appreciated by those skilled in the art that in the processes described above the functional groups (e.g. hydroxy, amino or carboxyl groups) of intermediate compounds may need to be protected by protecting groups. The final stage in the preparation of the compounds of the invention may involve the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The compounds of formula (I) above may be converted to a pharmaceutically-acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral HPLC). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are therefore indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (ADS).

Examples of these conditions are:

(1) (the respiratory tract) reversible obstructive airways diseases including asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease.

The compounds of the invention are also indicated for use as antimicrobial agents, and thus may be used in the treatment of diseases caused by pathogenic micro-organisms.

Accordingly, the present invention provides a compound of formula (I), or a pharmaceutically-acceptable salt or solvate thereof, as hereinbefore defined for use in therapy.

In another aspect, the invention provides the use of a compound of formula (I), or a pharmaceutically-acceptable salt or solvate thereof, as hereinbefore defined in the manufacture of a medicament for use in therapy.

The invention further provides a method of effecting immunosuppression which comprises administering to a patient a therapeutically effective amount of a compound of formula (I), or a pharmaceutically-acceptable salt or solvate thereof, as hereinbefore defined.

The invention still further provides a method of treating, or reducing the risk of, a reversible obstructive airways disease in a patient suffering from, or at risk of, said disease, which comprises administering to the patient a therapeutically effective amount of a compound of formula (I), or a pharmaceutically-acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically-acceptable salts and solvates thereof may be used on their own but will generally be administered in the form of a pharmaceutical composition in which the formula (1) compound/salt/solvate (active ingredient) is in association with a pharmaceutically-acceptable adjuvant, diluent or carrier. Depending on the mode of administration, the pharmaceutical composition will preferably comprise from 0.05 to 99%w (per cent by weight), more preferably less than 80%w, e.g. from 0.10 to 70%w, and even more preferably less than 50%w, of active ingredient, all percentages by weight being based on total composition.

Thus, the present invention also provides a pharmaceutical composition comprising a compound of formula (I), or a pharmaceutically-acceptable salt or solvate thereof, as hereinbefore defined, in association with a pharmaceutically-acceptable adjuvant, diluent or carrier.

The invention further provides a process for the preparation of a pharmaceutical composition of the invention which comprises mixing a compound of formula (I), or a pharmaceutically-acceptable salt or solvate thereof, as hereinbefore defined, with a pharmaceutically-acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will be illustrated by the subsequent examples in which the following abbreviations are used: m.p.=melting point, NMR=nuclear magnetic resonance, MS=mass spectrometry and h=hour(s).

EXAMPLE 1

6-(4-Methoxyphenylmethyl)-3-methylthieno[2,3-d] pyrimidine-2,4(1H,3H)-dione a) 3-(4-Methoxyphenyl)propanal A solution of 3-(4-methoxyphenyl)propan-1-ol (15.02 g) in dichloromethane (100 ml) was added to a stirred suspension of pyridinium chlorochromate (29 g) in dichloromethane (250 ml). The mixture was stirred for 2 hours then filtered through a kieselguhr pad. The residue was washed with ether (3×500 ml) and the combined liquors were evaporated under reduced pressure. The residual oil was purified by vacuum distillation to give the subtitle compound (6.81 g) as an oil.

MS (EI) 164 ($M^+$), 121 (BP)
$^1$H NMR (CDCl$_3$) δ2.75 (2H, t); 2.91 (2H, t); 3.79 (3H, s); 6.84 (2H, d); 7.12 (2H, d); 9.81 (1H, s).

b) Ethyl 2-amino-5-(4-methoxyphenylmethyl)-3-thiophenecarboxylate 3-(4-Methoxyphenyl)propanal (5.17 g) was added portionwise over 20 minutes to a stirred solution of ethyl cyanoacetate (3.4 g), sulfur (0.975 g) and triethylamine (3.00 ml) in dimethylformamide (10 ml). After a further 3 hours, the mixture was diluted with water (400 ml) and extracted with ethyl acetate (2×250 ml). The organic extracts were dried over anhydrous magnesium sulfate, filtered and evaporated under reduced pressure. The residue was purified by column chromatography over silica eluting with ethyl acetate:petroleum ether (1:3) to give the subtitle compound (7.08 g).

MS (EI) 291 ($M^+$)
$^1$H NMR (CDCl$_3$) δ1.33 (3H, t); 3.79 (3H, s); 3.85 (2H, s); 4.24 (2H, q); 5.79 (2H, s, br); 6.68 (1H, s); 6.84 (2H, d); 7.13 (2H, d).

c) N-[3-Ethoxycarbonyl-5-(4-methoxyphenylmethyl)-2-thienyl]-O-ethyl carbamate

Ethyl chloroformate (1.00 ml) was added to a stirred solution of ethyl 2-amino-5-(4-methoxyphenylmethyl)-3-thiophenecarboxylate (3.00 g) and pyridine (4.00 ml) in dichloromethane (30 ml) at 0–5° C. After 45 minutes, the mixture was washed with hydrochloric acid (10%, 50 ml). The aqueous phase was extracted with further dichloromethane (30 ml). Combined organic extracts were dried over anhydrous magnesium sulfate, filtered and evaporated under reduced pressure. The residue was purified by column chromatography over silica eluting with ethanol:dichloromethane gradient elution (1:19 to 1:3) to give the subtitle compound (5.61 g).

$^1$H NMR (CDCl$_3$) δ1.29–1.37 (6H, m); 3.79 (3H, s); 3.95 (2H, s); 4.22–4.32 (4H, m); 6.82–6.85 (3H, m); 7.15 (2H, d); 10.13 (1H, s, br).

d) 6-(4-Methoxyphenylmethyl)-3-methylthieno[2,3-d] pyrimidine-2,4(1H,3H)-dione

Methylamine (8 ml) was condensed into a cooled solution of N-[3-ethoxycarbonyl-5-(4-methoxyphenylmethyl)-2-thienyl]-O-ethyl carbamate (0.93 g) in ethanol (15 ml). The resulting solution was heated at 120° C. in a sealed bomb for 16 hours. The solvent was evaporated under reduced pressure and the residue was triturated with ether to give the title compound (0.31 g) as a solid.

MS (EI) 291 ($M^+$)
$^1$H NMR (DMSO-D$_6$) δ3.17 (3H, s); 3.73 (3H, s); 4.01 (2H, s); 6.87–6.91 (3H, m); 7.19 (2H, d); 12.10 (1H, s, br).

EXAMPLE 2

6-(4-Methoxyphenylmethyl)-3-methyl-1-(2-methyl-2-propenyl)thieno[2,3-d]pyrimidine-2,4(1H,3H)-dione 1-Bromo-2-methyl-2-propene (0.055 ml) was added to a stirred suspension of potassium carbonate (0.203 g) and 6-(4methoxyphenylmethyl)-3-methylthieno[2,3-d] pyrimidine-2,4(1H,3H)-dione (0.15 g) in acetone (5 ml). After 16 h at room temperature, the mixture was diluted with saturated aqueous sodium chloride solution and extracted with ethyl acetate. The organic extracts were dried over anhydrous magnesium sulfate, filtered and concentrated under reduced pressure. The residue was purified by column chromatography over silica, eluting with ethyl acetate:petroleum ether (1:3 then 3:7 then 7:13) to give the title compound (0.11 g).

m.p. 111° C.
MS (EI) 356 (M+)
$^1$H NMR (CDCl$_3$) δ1.75 (3H, s); 3.43 (3H, s); 3.81 (3H, s); 4.00 (2H, s); 4.48 (2H, s); 4.83 (1H, s); 4.98 (1H, s); 6.86 (2H, d); 7.02 (1H, s); 7.14 (2H, d).

EXAMPLE 3

1-(2-Methylpropyl)-6-(1-naphthalenylmethyl)thieno [2,3-d]pyrimidine-2,4(1H,3H)-dione a) 3-(1-naphthyl)propanoic acid 10% Palladium on carbon (1.00 g) was added to a suspension of 3-(1-naphthyl)acrylic acid (50.0 g) in tetrahydrofuran (500 ml). The mixture was hydrogenated at 6 atmospheres for 18 hours then filtered through a kieselguhr pad washing with ethyl acetate (3×100 ml). The filtrate was evaporated under reduced pressure to give the subtitle compound (50.0 g) as a solid.

$^1$H NMR (DMSO-D$_6$) δ2.65 (2H, t); 3.30 (2H, t); 7.37–7.46 (2H, m); 7.49–7.60 (2H, m); 7.79 (1H, d); 7.93 (1H, d); 8.07 (1H, d); 12.10 (1H, s, br).

b) Ethyl 2-amino-5-(1-naphthalenylmethyl)-3-thiophenecarboxylate

A solution of oxalyl chloride (7.40 ml) in anhydrous dichloromethane (50 ml) was added dropwise to a stirred suspension of 3-(1-naphthyl)propanoic acid (8.50 g) in anhydrous dichloromethane (100 ml) and dimethylformamide (0.1 ml). After a further 2 hours, the resulting solution was evaporated under reduced pressure and the residual oil dried in vacuo at 50° C. for 4 hours.

The oil was redissolved in anhydrous tetrahydrofuran (45 ml) and added to a mixture of 10% palladium on carbon (0.50 g) and anhydrous 2,6-lutidine (5.82 ml) in anhydrous tetrahydrofuran (30 ml). The mixture was hydrogenated at 2 atmospheres for 4 days and then filtered through a kieselguhr pad. The filtrate was evaporated under reduced pressure and the residual oil dried in vacuo to give a solid.

This solid was redissolved in anhydrous dimethylformamide (20 ml). Ethyl cyanoacetate (4.53 ml) and sulfur (1.36 ml) were added and the mixture stirred at 50° C., under nitrogen for 2 hours. Water (300 ml) followed by saturated sodium chloride solution (50 ml) were added and the mixture was extracted with ether (3×300 ml). The combined organic extracts were dried over anhydrous magnesium sulfate, filtered and evaporated under reduced pressure. The residue was purified by column chromatography over silica, eluting with ether:hexane (2:3) to give the subtitle compound (11.00 g).

MS (APCI) 312.1 ((M+H)$^+$), $^1$H NMR (DMSO-D$_6$) δ1.20 (3H, t); 4.12 (2H, q); 4.35 (2H, s); 6.56 (1H, s); 7.08 (2H, s, br); 7.41–7.56 (4H, m); 7.84 (1H, d); 7.90–7.96 (1H, m); 8.09–8.13 (1H, m).

c) Ethyl 2-(2-methylpropyl)amino-5-(1-naphthalenylmethyl)-3-thiophenecarboxylate Sodium borohydride (1.3 g) was added in 10 portions over 5 hours to a stirred solution of ethyl 2-amino-5-(1-naphthalenylmethyl)-3-thiophenecarboxylate (5.50 g) in 2-methylpropanoic acid (40 ml) at 0° C. The mixture was stirred at room temperature for 16 hours then further sodium borohydride (1.8 g) was added in 10 portions over 8 hours and stirring continued for a further 16 hours. The solution was poured into water (1000 ml), neutralized with sodium bicarbonate and extracted with ethyl acetate (2×500 ml). The organic extracts were dried over anhydrous magnesium sulfate, filtered and evaporated under reduced pressure. The residue was purified by column chromatography over silica, eluting with ether:hexane (1:3) to give the subtitle compound (6.20 g).

m.p. 57–59° C.

MS (APCI) 368.1 ((M+H)$^+$), $^1$H NMR (DMSO-D$_6$) δ0.86 (6H, d); 1.22 (3H, t); 1.66–1.92 (1H, m); 2.91 (2H, dd); 4.14 (2H, q); 4.40 (2H, s); 6.70 (1H, s); 7.43–7.57 (4H, m); 7.84 (1H, dd); 7.92–7.95 (1H, m); 8.11–8.14 (1H, m).

d) N'-Acetyl-N-(2-methylpropyl)-N-[3-ethoxycarbonyl-5-(1-naphthalenylmethyl)-2-thienyl]urea Acetyl chloride (1.08 ml) was added to a stirred suspension of silver cyanate (2.37 g) in anhydrous toluene (50 ml). After 1 hour, ethyl 2-(2-methylpropyl)amino-5-(1-naphthalenylmethyl)-3-thiophenecarboxylate (4.646 g) was added and stirring was continued for 16 hours. The mixture was filtered and the solid residue was washed with ether (50 ml). The combined liquors were evaporated under reduced pressure and the residue purified by column chromatography over silica, eluting with ether:hexane (1:1) to give the subtitle compound (5.05 g) as an oil.

MS (APCI) 453.1 ((M+H)$^+$), $^1$H NMR (CDCl$_3$) δ0.87 (6H, d); 1.29 (3H, t); 1.78–1.92 (1H, m); 2.44 (3H, s); 3.06–3.80 (2H, br); 4.24 (2H, q); 4.53 (2H, s); 7.09 (1H, s); 7.30 (1H, s, br); 7.41–7.58 (4H, m); 7.84 (1H, d); 7.90 (1H, dd); 7.99 (1H, dd).

e) 1-(2-Methylpropyl)-6-(1-naphthalenylmethyl)thieno[2,3-d]pyrimidine-2,4(1H,3H)-dione Sodium ethoxide (0.036 g) was added to a solution of N'-acetyl-N-(2-methylpropyl)-N-[3-ethoxycarbonyl-5-(1-naphthalenylmethyl)-2-thienyl]urea (0.20 g) in ethanol (4 ml). The mixture was stirred for 3 hours then further sodium ethoxide (0.036 g) was added. After a further 3 hours, the mixture was poured into hydrochloric acid (2M, 20 ml) and extracted with ethyl acetate (2×20 ml). The organic extracts were dried over anhydrous magnesium sulfate, filtered and evaporated under reduced pressure. The residual solid was recrystallised from ethyl acetate/hexane to give the title compound (0.105 g).

m.p. 189–190° C.

MS (APCI) 365.1 ((M+H)$^+$), $^1$H NMR (DMSO-D$_6$) δ0.84 (6H, d); 2.02–2.18 (1H, m); 3.57 (2H, d); 4.60 (2H, s); 7.01 (1H, s); 7.48–7.59 (4H, m); 7.87 (1H, dd); 7.95 (1H, dd); 8.16 (1H, dd); 11.34 (1H, s, br).

EXAMPLE 4

3-Methyl-1-(2-methylpropyl)-6-(1-naphthalenylmethyl)thieno[2,3-d]pyrimidine-2,4(1H,3H)-dione Sodium ethoxide (0.18 g) was added to a stirred solution of N'-acetyl-N-(2-methylpropyl)-N-[3-ethoxycarbonyl-5-(1-naphthalenylmethyl)-2-thienyl]urea (Example 3, step c), 0.30 g) in ethanol (6 ml). After 6 hours, iodomethane (0.165 ml) was added. After a further 16 hours iodomethane (0.165 ml) was added, After a further 24 hours, the reaction mixture was poured onto hydrochloric acid (2M, 30 ml) and extracted with ethyl acetate (2×30 ml). The organic extracts were dried over anhydrous magnesium sulfate, filtered and evaporated under reduced pressure. The residue was purified by column chromatography over silica, eluting with ether:hexane (1:1) and then triturated with ether to give the title compound (0.24 g).

m.p. 137–138° C.

MS (APCI) 379.1 ((M+H)$^+$), $^1$H NMR (CDCl$_3$) δ0.93 (6H, d); 2.18–2.32 (1H, m); 3.38 (3H, s); 3.68 (2H, d); 4.52 (2H, s); 7.04 (1H, t); 7.40–7.52 (4H, m); 7.82 (1H, d); 7.86–7.90 (1H, m); 7.95–8.02 (1H, m).

EXAMPLE 5

3-Methyl-1-(2-methylpropyl)-6-(1-naphthalenylmethyl)-5-[(2-pyridinyl)thio]thieno[2,3-d]pyrimidine-2,4(1H,3H)-dione n-Butyllithium (2.0M solution in hexanes, 0.32 ml) was added dropwise to a solution of diisopropylamine (0.093 ml) in anhydrous tetrahydrofuran (5 ml) at 0° C., under nitrogen. The solution was stirred for 5 minutes then cooled to −78° C. and a solution of 3-methyl-1-(2-methylpropyl)-6-(1-naphthalenylmethyl)thieno[2,3-d]pyrimidine-2,4(1H,3H)-dione (0.20 g) in anhydrous tetrahydrofuran (5 ml) was added. After 15 minutes, a solution of 2,2'-dipyridyl disulfide (0.145 g) in anhydrous tetrahydrofuran (2 ml) was added The mixture was stirred for a further 1 hour at −78° C. then allowed to warm to room temperature. The reaction mixture was poured onto saturated aqueous sodium bicarbonate solution (30 ml) and then extracted with ether (2×30 ml). The organic extracts were dried over anhydrous magnesium sulfate, filtered and evaporated under reduced pressure. The residue was purified by column chromatography over silica, eluting with acetone:hexane (1:2) and was then recrystallised from ethyl acetate/hexane to give the title compound (0.172 g).

m.p. 148–149° C.

MS (APCI) 488.1 ((M+H)$^+$), $^1$H NMR (CDCl$_3$) δ0.89 (6H, d); 2.10–2.25 (1H, m); 3.31 (3H, s); 3.63 (2H, d); 4.73 (2H, s); 7.05 (1H, dd); 7.17 (1H, d); 7.36 (1H, td); 7.40–7.58 (4H, m); 7.81 (1H, dd); 7.85 (1H, d); 7.98 (1H, d); 8.42–8.45 (1H, m).

EXAMPLE 6

5-[(3-Hydroxypropyl)thio]-3-methyl-1-(2-methylpropyl)-6-(1-naphthalenylmethyl)thieno[2,3-d]pyrimidine-2,4(1H,3H)-dione Prepared according to the procedure described in Example 5 from n-butyllithium (2.0M solution in hexanes, 0.32 ml) and diisopropylamine (0.093 ml) in anhydrous tetrahydrofuran (5 ml), 3-methyl-1-(2-methylpropyl)-6-(1-naphthalenylmethyl)thieno[2,3-d]pyrimidine-2,4(1H,3H)-dione (0.20 g) in anhydrous tetrahydrofuran (5 ml) and 3-{[dimethyl(1,1-dimethylethyl)silyl]oxy}propyl 4-methylphenylthiosulfonate (0.19 g, J. Med. Chem. 1995, 38, 2557) in anhydrous tetrahydrofuran (2 ml). The crude adduct was dissolved in tetrahydrofuran (6 ml) and treated with tetrabutylammonium fluoride hydrate (0.20 g). After 16 hours, the solution was diluted with water (30 ml) and extracted with ether (2×30 ml). The organic extracts were dried over anhydrous magnesium sulfate, filtered and evaporated under reduced pressure. The residue was purified by column chromatography over silica, eluting with ether and was then recrystallised from ethyl acetate/hexane to give the title compound (0.098 g).

m.p. 130–131° C.

MS (APCI) 469 ((M+H)$^+$), $^1$H NMR (CDCl$_3$) δ0.88 (6H, d); 1.90 (2H, quin); 2.10–2.24 (1H, m); 2.84 (1H, t); 3.17 (2H, t); 3.42 (3H, s); 3.63 (2H, d); 3.89 (2H, q); 4.78 (2H, s); 7.35 (1H, d); 7.44 (1H, t); 7.45–7.56 (2H, m); 7.82 (1H, d); 7.84–7.92 (1H, m); 8.01–8.07 (1H, m).

EXAMPLE 7

Methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate a) 4,4,4-Trimethoxybutyl para-toluenethiosulphonate A suspension of para-toluenethiosulphonic acid potassium salt (8.77 g), trimethyl 4-bromoorthobutyrate (8.00 g) and 18-crown-6 (10.24 g) in anhydrous tetrahydrofuran (60 ml) was ultrasonicated for 5 minutes then stirred at room temperature for 3 days. The mixture was poured into saturated aqueous sodium bicarbonate solution (200 ml) and extracted with ether (2×200 ml). The organic extracts were dried over anhydrous sodium sulfate, filtered and evaporated under reduced pressure to give the subtitle compound (10.52 g) as an oil.

$^1$H NMR (C$_6$D$_6$) δ1.57–1.62 (2H, m); 1.64–1.75 (2H, m); 1.86 (3H, s); 2.88 (2H, t); 3.06 (9H, s); 6.73 (2H, d); 7.84 (2H, d).

b) Methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate Prepared according to the procedure described in Example 5 from n-butyllithium (2.5M solution in hexanes, 0.77 ml) and diisopropylamine (0.277 ml) in anhydrous tetrahydrofuran (5 ml), 3-methyl-1-(2-methylpropyl)-6-(1-naphthalenylmethyl)thieno[2,3-d]pyrimidine-2,4(1H,3H)-dione (0.20 g) in anhydrous tetrahydrofuran (10 ml) and 4,4,4-trimethoxybutyl para-toluenethiosulphonate (0.799 g) in anhydrous tetrahydrofuran (5 ml). The reaction was quenched with hydrochloric acid (0.5M, 20 ml), diluted with ether (20 ml) and stirred for 10 minutes. The phases were separated and the aqueous phase extracted with further ether (20 ml). The combined organic extracts were dried over anhydrous magnesium sulfate, filtered and evaporated under reduced pressure. The residue was purified by column chromatography over silica, eluting with ether:hexane (1:1) to give the title compound (0.365 g) as a solid.

m.p. 111–112° C.

MS (APCI) 511.0 ((M+H)$^+$), $^1$H NMR (CDCl$_3$) δ0.87 (6H, d); 1.98 (2H, quin); 2.10–2.20 (1H, m); 2.52 (2H, t); 3.10 (2H, t); 3.42 (3H, s); 3.62 (2H, d); 3.67 (3H, s); 4.76 (2H, s); 7.35 (1H, d); 7.45 (1H, t); 7.48–7.55 (2H, m); 7.81 (1H, d); 7.86–7.92 (1H, m); 7.99–8.04 (1H, m).

EXAMPLE 8

4-[(1,2,3,4-Tetrahydro-3-methyl-1-(2-methylpropyl)-6-(1-naphthalenylmethyl)-2,4-dioxothieno[2,3-d]pyrimidin-5-yl)thio]butanoic acid Aqueous sodium hydroxide solution (1M, 4 ml) was added to a solution of methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate (0.382 g) in methanol (8 ml) and tetrahydrofuran (4 ml). The mixture was stirred at room temperature for 4 hours, diluted with water (50 ml), acidified with hydrochloric acid (2M) and extracted with an ether/ethyl acetate mixture (5:3, 80 ml). The organic extracts were dried over anhydrous magnesium sulfate, filtered and evaporated under reduced pressure. The residual solid was recrystallised from ethyl acetate/hexane to give the title compound (0.19 g).

m.p. 172–173° C.

MS (APCI) 497 ((M+H)$^+$), $^1$H NMR (DMSO-D$_6$) δ0.80 (6H, d); 1.78 (2H, quin); 1.97–2.15 (1H, m); 2.37 (2H, t); 3.04 (2H, t); 3.24 (3H, s); 3.58 (2H, d); 4.76 (2H, s); 7.42 (1H, d); 7.49 (1H, t); 7.53–7.59 (2H, m); 7.88 (1H, d); 7.96 (1H, dd); 8.06 (1H, d); 12.12 (1H, s, br).

EXAMPLE 9

Methyl 4-[(1,2,3,4-tetrahydro-3-methyl-1-(2-methylpropyl)-6-(1-naphthalenylmethyl)-2,4-dioxothieno[2,3-d]pyrimidin-5-yl)sulfinyl]butanoate Potassium peroxymonosulfate (0.163 g,) was added to a stirred suspension of methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate (0.246 g) in methanol (3 ml), tetrahydrofuran (3 ml) and water (3 ml). After 1 hour, the reaction mixture was poured into saturated aqueous sodium bicarbonate solution (20 ml) and extracted with ethyl acetate (2×20 ml) The organic extracts were dried over anhydrous magnesium sulfate, filtered and evaporated under reduced pressure. The residue was purified by column chromatography eluting with hexane:ethyl acetate (1:1) followed by trituration with ethyl acetate/hexane to give the title compound (0.80 g)

m.p. 160–161° C.

MS (APCI) 527.1 ((M+H)$^+$), $^1$H NMR (DMSO-D$_6$) δ0.77 (3H, d); 0.79 (3H, d); 1.95–2.09 (2H, m); 2.10–2.25 (1H, m); 2.56 (2H, t); 3.19 (3H, s); 3.20–3.33 (2H, m); 3.46 (1H, dd); 3.58–3.64 (4H, m); 4.74 (1H, d); 5.58 (1H, d); 7.50–7.59 (4H, m); 7.90 (1H, d); 7.97 (1H, d); 8.21 (1H, d).

EXAMPLE 10

Methyl 4-[(1,2,3,4-tetrahydro-3-methyl-1-(2-methylpropyl)-6-(1-naphthalenylmethyl)-2,4-dioxothieno[2,3-d]pyrimidin-5-yl)sulfonyl]butanoate 3-Chloroperoxybenzoic acid (57–86%, 0.366 g) was added to a solution of methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate (0.36 g) in dichloromethane (20 ml). After 1 hour, the solution was diluted with ethyl acetate (40 ml) and then washed with saturated aqueous sodium metabisulfite solution (20 ml) followed by saturated aqueous sodium bicarbonate solution (20 ml). The organic layer was dried over anhydrous magnesium sulfate, filtered and evaporated under reduced pressure. The residue was crystallised from ethyl acetate/hexane to give the title compound (0.182 g).

m.p. 122–124° C.

MS (APCI) 543.0 ((M+H)$^+$), $^1$H NMR (CDCl$_3$) δ0.81 (6H, d); 1.98–2.15 (1H, m); 2.30 (2H, quin); 2.61 (2H, t); 3.40 (3H, s); 3.54 (2H, d); 3.71 (3H, s); 3.94 (2H, t); 5.10 (2H, s); 7.43–7.58 (4H, m); 7.86–7.94 (3H, m).

EXAMPLE 11

4-[(1,2,3,4-Tetrahydro-3-methyl-1-(2-methypropyl)-6-(1-naphthalenylmethyl)-2,4-dioxothieno[2,3-d]pyrimidin-5-yl)sulfonyl]butanoic acid Sodium hydroxide solution (1M, 1 ml) was added to a stirred suspension of methyl 4-[(1,2,3,4-tetrahydro-3-methyl-1-(2-methylpropyl)-6-(1-naphthalenylmethyl)-2,4-dioxothieno[2,3-d]pyrimidin-5-yl)sulfonyl]butanoate (0.10 g) in methanol (3 ml) and tetrahydofuran (3 ml). After 4 hours, the reaction mixture was diluted with water (20 ml), acidified with hydrochloric acid (2M) and extracted with ethyl acetate (2×30 ml). The organic extracts were evaporated under reduced pressure. The residue was partitioned between ether (30 ml) and aqueous sodium hydroxide solution (0.1M, 30 ml). The aqueous phase was acidified with hydrochloric acid (2M) and extracted with ethyl acetate (2×30 ml). The organic extracts were dried over anhydrous magnesium sulfate, filtered and evaporated under reduced pressure. The residue was triturated with ethyl acetate/hexane to give the title compound (0.028 g).

m.p. 174–175° C.

MS (APCI) 529.0 ((M+H)$^+$), $^1$H NMR (DMSO-D$_6$) δ0.77 (6H, d); 1.92–2.05 (3H, m); 2.43 (2H, t); 3.24 (3H, s); 3.55 (2H, d) 3.85 (2H, t); 5.10 (2H, s); 7.46–7.61 (4H, m); 7.95 (1H, d); 7.97–8.04 (2H, m); 12.22 (1H, s, br).

EXAMPLE 12

6-Benzyl-3methyl-1-(2-methylpropyl)thieno[2,3-d]pyrimidine-2,4(1H,3H)-dione a) Ethyl 2-amino-5-(phenylmethyl)thiophene-3-carboxylate Triethylamine (10.40 ml) was added to a solution of 3-phenylpropanal (10.0 g), ethyl cyanoacetate (7.95 ml) and sulfur (2.40 g) in dimethylformamide (30 ml). The mixture was heated at 50° C. under nitrogen for 3 hours, then diluted with water (350 ml) and extracted with diethyl ether four times. The organic extracts were dried over anhydrous magnesium sulfate, filtered and evaporated under reduced pressure. The residue was purified by column chromatography eluting with diethyl ether:isohexane (1:3) to give the subtitle compound (14.2 g).

MS (APCI) 262 ((M+H)$^+$)

$^1$H NMR (CDCl$_3$) δ1.33 (3H, t); 3.91 (2H, s); 4.25 (2H, q); 5.78 (2H, bs); 6.70 (1H, s); 7.20–7.33 (5H, m)

b) Ethyl 2-(2-methylpropylamino)-5-(phenylmethyl)thiophene-3-carboxylate

Sodium borohydride (3.0 g) was added in 6 portions over 3 hours to a stirred solution of ethyl 2-amino-5-(phenylmethyl)thiophene-3-carboxylate in 2-methylpropanoic acid under nitrogen. The mixture was stirred at room temperature for 20 hours and was then diluted with water, neutralized with sodium bicarbonate and extracted with ethyl acetate four times. The organic extracts were dried over anhydrous magnesium sulfate, filtered and evaporated under reduced pressure. The residue was purified by column chromatography, eluting with diethyl ether:isohexane (1:19) to give the subtitle compound (2.80 g).

MS (APCI) 318 ((M+H)$^+$)

$^1$H NMR (CDCl$_3$) δ0.96 (6H, d); 1.32 (3H, t); 1.93 (1H, m); 2.97 (2H, dd); 3.92 (2H, s); 4.23 (2H, q); 6.75 (1H, s); 7.20–7.34 (5H, m); 7.46 (1H, m)

c) N'-Acetyl-N-(2-methylpropyl)-N-[3-ethoxycarbonyl-5-(phenylmethyl)-2-thienyl]urea Acetyl chloride (0.69 ml) was added to a stirred suspension of silver cyanate (1.51 g) in anhydrous toluene (30 ml) under nitrogen. After 1 hour, ethyl 2-(2-methylpropylamino)-5-(phenylmethyl)thiophene-3-carboxylate (2.55 g) was added and stirring was continued for 20 hours. The mixture was filtered and the solid residue was washed with diethyl ether. The combined liquors were evaporated under reduced pressure and the residue was purified by column chromatography eluting with diethyl ether:isohexane (1:1) to give the subtitle compound (3.08 g).

MS (APCI) 403 ((M+H)$^+$)

$^1$H NMR (CDCl$_3$) δ0.88 (6H, d); 1.31 (3H, t); 1.92 (1H, m); 2.46 (3H, s); 2.80–3.90 (2× 1H, 2 vbs); 4.08 (2H, s); 4.27 (2H, q); 7.08 (1H, s); 7.25–7.39 (5H, m); 7.46 (1H, m)

d) 3-Methyl-1-(2-methylpropyl)-6-(phenylmethyl)thieno[2,3-d]pyrimidine-2,4(1H,3H)-dione Sodium ethoxide (1.96 g) was added to a solution of N'-acetyl-N-(2-methylpropyl)-N-[3-ethoxycarbonyl-5-(phenylmethyl)-2-thienyl]urea (2.90 g) in ethanol (40 ml) under nitrogen. The mixture was stirred for 20 hours then iodomethane (1.80 ml) was added. The mixture was heated to reflux for 3 hours and then allowed to cool to room temperature and evaporated under reduced pressure. The residue was diluted with water and extracted with ethyl acetate twice. The organic extracts were dried over anhydrous magnesium sulfate, filtered and evaporated under reduced pressure. The residue was purified by column chromatography eluting with diethyl ether:isohexane (1:1) to give an oil which was recrystallised from diethyl ether/isohexane to give the title compound (1.70 g).

m.p. 72–3° C.

MS (APCI) 329 ((M+H)$^+$)

$^1$H NMR (CDCl$_3$) δ0.95 (6H, d); 2.28 (1H, m); 3.41 (3H, s); 3.72 (2H, d); 4.07 (2H, s); 7.05 (1H, s); 7.23–7.37 (5H, m)

EXAMPLE 13

3-Methyl-1-(1-methylethyl)-6-(phenylmethyl)thieno[2,3-d]pyrimidine-2,4(1H,3H)dione a) 2-(1-methylethylamino)-5-(phenylmethyl)thiophene-3-carboxylic acid, ethyl ester To a solution of 2-amino-5-(phenylmethyl)thiophene-3-carboxylic acid, ethyl ester (2.61 g) and 4-methylbenzenesulfonic acid (30 mg) in dry toluene (50 ml) was added 2,2-dimethoxypropane. The solution was heated to reflux for 5 hours and then allowed to cool to ambient temperature. A solution of sodium borohydride (800 mg) in ethanol (100 ml) was added to the solution and the mixture was stirred at room temperature under nitrogen for 24 hours. The mixture was diluted with water and then extracted thrice with ethyl acetate. The combined organic extracts were washed with brine and then dried over anhydrous magnesium sulfate, filtered and evaporated under reduced pressure to give an oil. The residue was purified by column chromatography over silica, eluting with diethyl ether:isohexane (1:19) to give the subtitle compound (550 mg).

MS (APCI) 304 ((M+H)$^+$)

$^1$H NMR (CDCl$_3$) δ1.25 (6H, d); 1.31 (3H, t); 3.41 (1H, m); 3.93 (2H, s); 4.22 (2H, q); 6.74 (1H, s); 7.20–7.33 (5H, m)

b) N'-acetyl-N-(1-methylethyl)-N-[3-ethoxycarbonyl-5-(phenylmethyl)-2-thienyl]urea Prepared from 2-(1-methylethylamino)-5-(phenylmethyl)thiophene-3-carboxylic acid, ethyl ester (550 mg), silver cyanate (340 mg) and acetyl chloride (0.155 ml) following the method of Example 12, step c) to give the subtitle compound.

MS (APCI) 389 ((M+H)$^+$)

c) 3-methyl-1-(1-methylethyl)-6-(phenylmethyl)thieno[2,3-d]pyrimidine-2,4(1H,3H)-dione Prepared from N'-acetyl-N-(1-methylethyl)-N-[3-ethoxycarbonyl-5-(phenylmethyl)-2-thienyl]urea (700 mg), sodium ethoxide (400 mg) and iodomethane (0.45 ml) following the method of Example 12, step d) to give the title compound.

m.p. 91–3° C.

MS (APCI) 315 ((M+H)$^+$) $^1$H NMR (CDCl$_3$) δ1.55 (6H, d); 3.38 (3H, s); 4.07 (2H, s); 4.60 (1H, bs);

7.07 (1H, s); 7.23–7.37 (5H, m)

EXAMPLE 14

6-[(1-Hydroxy-1-phenyl)methyl]-3-methyl-1-(2-methylpropyl)thieno[2,3-d]pyrimidine-2,4(1H,3H)-dione A solution of 3-methyl-1-(2-methylpropyl)-6-(phenylmethyl)thieno[2,3-d]pyrimidine-2,4(1H,3H)-dione (Example 12, 0.150 g) and N-bromosuccinimide (0.090 g) in anhydrous chloroform (5 ml) was heated to reflux under nitrogen for 2 hours. The mixture was evaporated under reduced pressure and the residue was purified by column chromatography eluting with diethyl ether:isohexane (1:1) to give the title compound (0.085 g).

m.p. 140–2° C.

MS (APCI) 345 ((M+H)$^+$)

$^1$H NMR (CDCl$_3$) δ0.97 (6H, d); 2.31 (1H, m); 2.57 (1H, d); 3.39 (3H, s); 3.77 (2H, ddd); 5.97 (1H, d); 7.03 (1H, s); 7.33–7.46 (5H, m)

EXAMPLE 15

(±) 5-[(2-Hydroxypropyl)thio]-3-methyl-1-(2-methylpropyl)-6-(1-naphthalenylmethyl)thieno[2,3-d]pyrimidine-2,4(1H,3H)-dione a) (±) and meso Bis2-hydroxypropyldisulfide 1-Mercaptopropan-2-ol (2 ml) was dissolved in dichloromethane (10 ml). Sodium bicarbonate (2.67 g) and water (10 ml) were added. The suspension was stirred vigorously and cooled in an ice bath. A solution of bromine (0.59 ml) in dichloromethane (5 ml) was added dropwise to the suspension. The mixture was stirred for 10 minutes after addition was complete, then the phases were separated. The aqueous phase was extracted with dichloromethane, the dichloromethane phases were combined, then dried, filtered and evaporated to give the subtitle compound (2.56 g).

$^1$H NMR (CDCl$_3$) δ1.29 (6H, d), 2.33 (2H, br), 2.67–2.75 (2H, m), 2.83–2.92 (2H, m), 4.05–4.12 (2H, m).

b) (±) and meso Bis 2-[(1,1-dimethylethyl)(dimethyl)silyloxy]propyldisulfide (±) And meso bis 2-hydroxypropyldisulfide (2.56 g) was dissolved in dimethyformamide (20 ml). Imidazole (1.60 g) and dimethyl(1,1-dimethylethyl)silyl chloride (3.46 g) were added and the resulting solution was stirred overnight. The reaction mixture was poured into water (100 ml) and extracted thrice with ether. The ether extracts were combined, washed with brine, dried, filtered and evaporated. Chromatography, eluting with isohexane:ether (99:1), gave the subtitle compound (3.90 g).

$^1$H NMR (CDCl$_3$) δ0.08 (6H, s), 0.09 (6H, s), 0.89 (18H, s), 1.24 (6H, d), 2.63–2.70 (2H, m), 2.79–2.87 (2H, m), 4.00–4.07 (2H, m).

c) (±) 5-[(2-Hydroxypropyl)thio]-3-methyl-1-(2methylpropyl)-6-(1-naphthalenylmethyl)thieno[2,3-d]pyrimidine-2,4(1H,3H)-dione 3-Methyl-1-(2-methylpropyl)-6-(1-naphthalenylmethyl)thieno[2,3-d]pyrimidine-2,4(1H,3H)-dione (Example 2) (220 mg) was dissolved in tetrahydrofuran (1 ml) and cooled to –78°. LDA (1M solution in tetrahydrofuran/hexane) was added dropwise until a red colour persisted. The solution was stirred for 1 h then a solution of (±) and meso bis 2-[dimethyl(1,1-dimethylethyl)silyloxy]propyldisulfide (298 mg) in tetrahydrofuran (3 ml) was added and the solution was allowed to warm to 0° C. After 65 minutes sodium bicarbonate (aqueous) was added and the mixture was extracted thrice with ethyl acetate. The ethyl acetate phases were combined, washed with brine; dried, filtered and evaporated. Chromatography eluting with isohexane:ethyl acetate (9:1 to 4:1) gave the silyl ether of the title compound (MS (+ve APCI) 583 (M+H)$^+$). The silyl ether was dissolved in acetonitrile (3 ml), hydrofluoric acid (40% aqueous, 0.6 ml) was added and the solution was stirred for 40 minutes. Sodium bicarbonate (aqueous) was added and the reaction mixture was extracted thrice with ethyl acetate. The ethyl acetate phases were combined, washed with brine, dried, filtered and evaporated. Chromatography, eluting with isohexane:ethyl acetate (3:1) changing to ethyl acetate followed by HPLC (isohexane:ethyl acetate 50:50 to 0:100), gave the title compound (28 mg).

m.p. 126–128°

MS (+ve APCI) 469 ((M+H)$^+$)

$^1$H NMR (DMSO d-6) δ0.81 (6H, d), 1.17 (3H, d), 1.98–2.11 ($^1$H, m), 2.89–2.95 (1H, m), 3.00–3.06 (1H, m), 3.25 (3H, s), 3.59 (2H, d), 3.70–3.81 (1H, m), 4.79 (2H, s), 4.84 (1H, d), 7.41 (1H, d), 7.49 (1H, t), 7.52–7.58 (2H, m), 7.88 (1H, d), 7.93–7.98 (1H, m) and 8.08–8.11 (1H, m).

EXAMPLE 16

1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-carboxamide a) 1,2,3,4-Tetrahydro-3-methyl-1-(2-methylpropyl)-6-(1-naphthalenylmethyl)-2,4-dioxothieno[2,3-d]pyrimidine-5-carboxylic acid n-Butyllithium (2.0M solution in hexanes, 1.90 ml) was added dropwise to a solution of diisopropylamine (0.069 ml) in anhydrous tetrahydrofuran (30 ml) at 0° C., under nitrogen. The solution was stirred for 5 minutes then cooled to –78° C. and a solution of 3-methyl-1-(2-methylpropyl)-6-(1-naphthalenylmethyl)thieno[2,3-d]pyrimidine-2,4(1H, 3H)-dione (1.50 g) in anhydrous tetrahydrofuran (15 ml) was added dropwise. After 15 minutes, the flask was transferred to a sealed bomb containing carbon dioxide pellets (2 g) and heated to 50° C. for 18 hours. The reaction mixture was cooled to room temperature then added to aqueous sodium hydroxide solution (0.25M, 75 ml) and washed with ether (2×75 ml). The aqueous layer was acidified with concentrated hydrochloric acid and extracted with ether (2×75 ml). The organic extracts were dried over anhydrous magnesium sulfate, filtered and evaporated under reduced pressure. The residue was purified by column chromatography over silica, eluting with isohexane:ethyl acetate (3:1) containing 1% acetic acid, to give the subtitle compound (0.337 g) as a solid.

MS (+ve APCI) 423 ((M+H)$^+$)MS.

$^1$H NMR (DMSO d$_6$) δ0.79 (6H, d), 1.96–2.10 (1H, m), 3.25 (3H, s), 3.58 (2H, d), 4.74 (2H, d), 7.49–7.55 (4H, m), 7.88–7.91 (1H, m), 7.95–7.98 (1H, m), 8.09–8.12 (1H, m).

b) 1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-carboxamide To a solution of 1,2,3,4-tetrahydro-3-methyl-1-(2-methylpropyl)-6-(1-naphthalenylmethyl)-2,4-dioxothieno[2,3-d]pyrimidine-5-carboxylic acid (50 mg) and 2-aminoethanol (14 µl) in dichloromethane (2ml) was added 1-hydroxybenzotriazole hydrate (48 mg) followed by 1-(3-dimethylaminopropyl)-3-ethylcarbodiimide hydrochloride (45 mg). The reaction mixture was stirred at room temperature for 18 hours then hydrochloric acid (1M, 20 ml) was added and the mixture was extracted with ether (30 ml). The organic extracts were washed with water, then with 1M sodium hydroxide solution, dried over anhydrous magnesium sulfate, filtered and evaporated under reduced pressure. The residue was recrystallised from ethyl acetate:isohexane to give the title compound (28 mg).

m.p. 193–194° C.

MS (+ve APCI) 466 ((M+H)$^+$)

$^1$H NMR (CDCl$_3$) δ0.84 (6H, d), 2.05–2.20 (1H, m), 3.41 (3H, s), 3.57–3.70 (5H, m), 3.91 (2H, q), 4.92 (2H, s), 7.42–7.52 (4H, m), 7.82–7.90 (2H, m), 8.04–8.08 (1H, m), 8.38 (1H, t, br).

The following compounds were prepared according to the method of Example 16 using 1,2,3,4-tetrahydro-3-methyl-1-(2-methylpropyl)-6-(1-naphthalenylmethyl)-2,4-dioxothieno[2,3-d]pyrimidine-5-carboxylic acid (Example 15a) and the appropriate amine.

EXAMPLE 21

2-{[1,2,3,4-Tetrahydro-3-methyl-1-(2-methylpropyl)-6-(1-naphthalenylmethyl)-2,4-dioxothieno[2,3-d]pyrimidin-5-yl]carboxamnido}acetic acid Oxalyl chloride (0.092 ml) was added to a solution of 1,2,3,4-tetrahydro-3-methyl-1-(2-methylpropyl)-6-(1-naphthalenylmethyl)-2,4-dioxothieno[2,3-d]pyrimidine-5-carboxylic acid (Example 15a, 222 mg) and dimethylformamide (0.01 ml) in anhydrous dichloromethane (5 ml) at room temperature. After 2 hours, the solution was evaporated under reduced pressure to give 1,2,3,4-tetrahydro-3-methyl-1-(2-methylpropyl)-6-(1-naphthalenylmethyl)-2,4-dioxothieno[2,3-d]pyrimidine-5-carbonyl chloride as an oil. A solution of this oil (58 mg) in anhydrous dichloromethane (2 ml) was added to a stirred mixture of glycine methyl ester hydrochloride (29 mg) and triethylamine (0.037 ml) in anhydrous dichloromethane (1 ml) at room temperature. After 1 hour, ethyl acetate (25 ml) and 2M hydrochloric acid were added. The organic layer was washed with water then with saturated sodium hydrogen carbonate solution, dried over anhydrous magnesium sulfate, filtered and evaporated under reduced pressure The residue was dissolved in a mixture of tetrahydrofuran (4 ml), methanol (2 ml) and 1M sodium hydroxide solution (1 ml). After 2 hours, water (20 ml) was added and the solution was extracted with ether (20 ml). The aqueous layer was acidified with hydrochloric acid and then extracted with ethyl acetate (3×20 ml). The organic extracts were dried over anhydrous magnesium sulfate, filtered and evaporated under reduced pressure. The residue was recrystallised from ethyl acetate:isohexane to give the title compound (42 mg).

m.p. 218–219° C.

MS (+ve APCI) 480 ((M+H)$^+$)

$^1$H NMR (CDCl$_3$/DMSO d$_6$) δ0.83 (6H, d), 2.06–2.15 (1H, m), 3.41 (3H, s), 3.59 (2H, d), 4.23 (2H, d), 5.00 (2H, s), 7.43–7.54 (4H, m), 7.80–7.90 (2H, m), 8.01–8.06 (1H, m) 9.73 (1H, t).

The following Examples were prepared according to the method of Example 21 using 1,2,3,4-tetrahydro-3-methyl-1-(2-methylpropyl)-6-(1-naphthalenylmethyl)-2,4-dioxothieno[2,3-d]pyrimidine-5-carbonyl chloride (prepared in Example 19) and the appropriate amine (excluding the hydrolysis step for Examples 23 and 24).

EXAMPLE 25

1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-sulfonamide a) Lithium 1,2,3,4-Tetrahydro-3-methyl-1-(2-methylpropyl)-6-(1-naphthalenylmethyl)-2,4-dioxothieno[2,3-d]pyrimidine-5-sulfinate A solution of lithium diisopropylamide (3.52 mmol) in anhydrous tetrahydrofuran (10 ml) was added dropwise to a solution of of 3-methyl-1-(2-methylpropyl)-6-(1-naphthalenylmethyl)thieno[2,3-d]pyrimidine-2,4(1H,3H)-dione (1.00 g) in anhydrous tetrahydrofuran (20 ml) at −78° C. under nitrogen. After 15 minutes, sulfur dioxide was bubbled through the reaction mixture which was warmed to room temperature over 30 minutes. Nitrogen was then bubbled through the solution for 10 minutes. The precipitated solid was filtered, washed with ether and dried in vacuo at 50° C. to give the subtitle compound (1.20 g).

MS (+ve APCI) 425 ((M+H−HOLi)$^+$)

$^1$H NMR (DMSO d$_6$) δ0.75 (6H, d), 1.85–2.06 (1H, m), 3.21 (3H, s), 3.50 (2H, d), 5.22 (1H, s), 7.43–7.51 (3H, m), 7.55 (1H, d), 7.83 (1H, d), 7.90 (1H, dd), 8.54 (1H, dd).

b) 1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-sulfonamide N-Chlorosuccinimide (52 mg) was added to a rapidly stirred suspension of lithium 1,2,3,4-tetrahydro-3-methyl-1-(2-methylpropyl)-6-(1-naphthalenylmethyl)-2,4-dioxothieno[2,3-d]pyrimidine-5-sulfinate (200 mg) in dichloromethane (8 ml) and 0.22M hydrochloric acid (9 ml). After 1 hour, further N-chlorosuccinimide (26 mg) was added. After 1 hour, water (30 ml) and dichloromethane (30 ml) were added and the phases were separated. The aqueous phase was extracted with dichloromethane (2×10 ml). The combined organic extracts were treated with ethanolamine (0.071 ml). After 30 minutes, the solution was washed with saturated sodium hydrogen carbonate solution, dried over anhydrous magnesium sulfate, filtered and evaporated under reduced pressure. The residue was purified by column chromatography over silica, eluting with ether to give the title compound (120 mg) as a foam.

MS (+ve APCI) 502 ((M+H)$^+$)

$^1$H NMR (CDCl$_3$) δ0.82 (6H, d), 2.01–2.16 (1H, m), 3.32 (2H, q), 3.41 (3H, s), 3.79–3.85 (2H, m), 5.05 (2H, s), 7.41–7.56 (4H, m), 7.59 (1H, t), 7.83–7.98 (3H, m).

EXAMPLE 26

5-[(3-Methoxyphenyl)thio]-3-methyl-1-(2-methylpropyl)-6-(1-naphthalenylmethyl)thieno[2,3-d]pyrimidine-2,4-(1H,3H)-dione A solution of lithium diisopropylamide (3.09 mmol) in anhydrous tetrahydrofuran (10 ml) was added dropwise to a solution of 3-methyl-1-(2-methylpropyl)-6-(1-naphthalenylmethyl)thieno[2,3-d]pyrimidine-2,4(1H,3H)-dione (1.00 g) in anhydrous tetrahydrofuran (25 ml) at −78° C. under nitrogen. After 15 minutes, bis-(3-methoxyphenyl)

disulfide (J. Amer. Chem. Soc.; 75; 1953; 5736) (0.88 g) was added and the mixture was allowed to warm to room temperature. The mixture was added to saturated sodium hydrogen carbonate solution (100 ml) and extracted with ether (2×100 ml). The organic extracts were dried over anhydrous magnesium sulfate, filtered and evaporated under reduced pressure. The residue was purified by column chromatography over silica, eluting with isohexane:ether (1:1) to give the title compound (1.00 g) as an oil.

MS (+ve APCI) 517 ((M+H)$^+$)

$^1$H NMR (CDCl$_3$) δ0.88 (6H, d), 2.13–2.22 (1H, m), 3.34 (3H, s), 3.62 (2H, d), 3.76 (3H, s), 4.71 (2H, s), 6.71 (1H, dt), 6.79 (1H, t), 6.81 (1H, d), 7.20 (1H, t), 7.37–7.52 (4H, m), 7.81 (1H, d), 7.86 (1H, d), 7.89 (1H, d).

EXAMPLE 27

5-[(3-Hydroxyphenyl)thio]-3-methyl-1-(2-methylpropyl)-6-(1-naphthalenylmethyl)thieno[2,3-d]pyrimidine-2,4-(1H,3H)-dione Boron tribromide (1M solution in dichloromethane, 5.63 ml) was added to a stirred solution of 5-[(3-methoxyphenyl)thio]-3-methyl-1-(2-methylpropyl)-6-(1-naphthalenylmethyl)thieno[2,3-d]pyrimidine-2,4-(1H,3H)-dione (Example 26, 0.97 g) in anhydrous dichloromethane (50 ml) at 0° C. under nitrogen. After 1 hour, saturated sodium hydrogen carbonate solution (100 ml) was added and the mixture was extracted with ethyl acetate (2×100 ml). The organic extracts were dried over anhydrous magnesium sulfate, filtered and evaporated under reduced pressure. The residue was purified by column chromatography over silica, eluting with ethyl acetate:isohexane (3:2) and then recrystallised from ethyl acetate:isohexane to give the title compound (0.468 g).

m.p. 200–201° C.

MS (+ve APCI) 503 ((M+H)$^+$)

$^1$H NMR (DMSO d$_6$) δ0.82 (6H, d), 2.00–2.11 (1H, m), 3.17 (3H, s), 3.61 (2H, d), 4.73 (2H, s), 6.56 (1H, t), 6.58 (1H, dt), 6.64 (1H, dt), 7.11 (1H, t), 7.35 (1H, td), 7.45–7.52 (3H, m), 7.86–7.90 (2H, m), 7.94 (1H, d), 9.49 (1H, s).

EXAMPLE 28

5-[(3-Hydroxyphenyl)sulfinyl]-3-methyl-1-(2-methylpropyl)-6-(1-naphthalenylmethyl)thieno[2,3-d]pyrimidine-2,4-(1H,3H)-dione 3-Chloroperoxybenzoic acid (0.12 g) was added to a solution of 5-[(3-hydroxyphenyl)thio]-3-methyl-1-(2-methylpropyl)-6-(1-naphthalenylmethyl)thieno[2,3-d]pyrimidine-2,4-(1H,3H)-dione (Example 27, 0.20 g) in dichloromethane (5 ml). After 2 hours, ethyl acetate (50 ml) was added and the solution was washed with saturated sodium bisulfite solution (25 ml), then with saturated sodium hydrogen carbonate solution (25 ml), then with brine (25 ml). The organic layer was dried over anhydrous magnesium sulfate, filtered and evaporated under reduced pressure. The residue was purified by preparative normal-phase HPLC with dichloromethane:ethanol gradient elution then recrystallised from ethyl acetate:isohexane to give the title compound (0.05 g).

m.p. 242–243° C.

MS (+ve APCI) 519 ((M+H)$^+$)

$^1$H NMR (DMSO d$_6$) δ0.74 (3H, d), 0.75 (3H, d), 1.88–2.02 (1H, m), 3.25 (3H, s), 3.49 (2H, d), 4.58 (1H, d), 5.37 (1H, d), 6.95 (1H, dt), 7.24–7.36 (3H, m), 7.42 (1H, t), 7.45–7.55 (3H, m), 7.67 (1H, d), 7.89 (1H, d), 7.94 (1H, d).

EXAMPLE 29

5-[(3-Hydroxyphenyl)sulfonyl]-3-methyl-1-(2-methylpropyl)-6-(1-naphthalenylmethyl)thieno[2,3-d]pyrimidine-2,4-(1H,3H)-dione 3-Chloroperoxybenzoic acid (50 mg) was added to a solution of 5-[(3-hydroxyphenyl)sulfinyl]-3-methyl-1-(2-methylpropyl)-6-(1-naphthalenylmethyl)thieno[2,3-d]pyrimidine-2,4-(1H,3H)-dione (Example 28, 80 mg) in dichloromethane (2 ml). After 2 hours, ethyl acetate (25 ml) was added and the solution was washed with saturated sodium bisulfite solution (10 ml), then with saturated sodium hydrogen carbonate solution (10 ml), then with brine (10 ml). The organic layer was dried over anhydrous magnesium sulfate, filtered and evaporated under reduced pressure. The residue was recrystallised from ethyl acetate:isohexane to give the title compound (24 mg).

m.p. 209–210° C.

MS (+ve APCI) 535 ((M+H)$^+$)

$^1$H NMR (DMSO d$_6$) δ0.76 (6H, d), 1.89–2.01 (1H, m), 3.11 (3H, s), 3.52 (2H, d), 5.25 (2H, s), 7.05 (1H, dt), 7.38–7.68 (7H, m), 7.94 (1H, dd), 7.99–8.07 (2H, m).

EXAMPLE 30

3-Methyl-1-(2-methylpropyl)-6-(1-naphthalenylmethyl)-5-[(3-nitrophenyl)thio]thieno[2,3-d]pyrimidine-2,4-(1H, 3H)-dione A solution of lithium diisopropylamide (3.63 mmol) in anhydrous tetrahydrofuran (5.5 ml) was added dropwise to a solution of 3-methyl-1-(2-methylpropyl)-6-(1-naphthalenylmethyl)thieno[2,3-d]pyrimidine-2,4(1H,3H)-dione (1.00 g) in anhydrous tetrahydrofuran (20 ml) at −78° C. under nitrogen. After 15 minutes, bis(3-nitrophenyl) disulfide (0.90 g) was added and the mixture was warmed to room temperature over 1 hour. Saturated sodium hydrogen carbonate solution (100 ml) was added and the mixture was extracted with ether (2×100 ml). The organic extracts were dried over anhydrous magnesium sulfate, filtered and evaporated under reduced pressure. The residue was purified by column chromatography over silica, eluting with ethyl acetate:isohexane (1:1) to give partially purified material (1.40 g). A portion of this material (0.20 g) was further purified by preparative normal-phase HPLC with dichloromethane:ethanol gradient elution and then recrystallised from ethyl acetate:isohexane to give the title compound (22 mg).

m.p. 144–145° C.

MS (+ve APCI) 532 ((M+H)$^+$)

$^1$H NMR (CDCl$_3$) δ0.91 (6H, d), 2.12–2.28 (1H, m), 3.31 (3H, s), 3.66 (2H, d), 4.75 (2H, s), 7.36–7.53 (5H, m), 7.56 (1H, dt), 7.82 (1H, d), 7.88 (1H, d), 7.92 (1H, d), 7.95 (1H, t), 8.00 (1H, dt).

EXAMPLE 31

5-[(3-Aminophenyl)thio]-3-methyl-1-(2-methylpropyl)-6-(1-naphthalenylmethyl)thieno[2,3-d]pyrimidine-2,4-(1H,3H)-dione A suspension of the partially purified 3-methyl-1-(2-methylpropyl)-6-(1-naphthalenylmethyl)-5-[(3-nitrophenylthio]thieno[2,3-d]pyrimidine-2,4-(1H,3H)-dione (Example 30, 1.20 g), iron powder (0.59 g) and ammonium chloride (0.56 g) in ethanol (5 ml) and water (5 ml) was heated at reflux for 2 hours, then cooled to room temperature. 2M Sodium hydroxide solution (50 ml) was added and the mixture was stirred for 30 minutes. The resulting solution was decanted from insoluble solid. The solid and solution were in turn extracted with ethyl acetate (3×50 ml). The combined organic extracts were dried over anhydrous magnesium sulfate, filtered and evaporated under reduced pressure. The residue was purified by column chromatography over silica, eluting with ether:isohexane (2:1) followed by recrystallisation from ethyl acetate:isohexane to give the title compound (0.41 g).

m.p. 149–150° C.

MS (+ve APCI) 502 ((M+H)$^+$)

$^1$H NMR (CDCl$_3$) δ0.88 (6H, d), 2.10–2.23 (1H, m), 3.35 (3H, s), 3.62 (2H, d), 3.63 (2H, s), 4.71 (2H, s), 6.48 (1H, dt), 6.59 (1H, t), 6.64 (1H, dt), 7.06 (1H, t), 7.37–7.50 (4H, m), 7.80–7.92 (3H, m).

EXAMPLE 32

5-{[3-{(Bis-methanesulfonyl)amino}phenyl]thio}-3-methyl-1-(2-methylpropyl)-6-(1-naphthalenylmethyl)thieno[2,3-d]pyrimidine-2,4-(1H,3H)-dione Methanesulfonyl chloride (0.028 ml) was added to a solution of 5-[(3-aminophenyl)thio]-3-methyl-1-(2-methylpropyl)-6-(1-naphthalenylmethyl)thieno[2,3-d]pyrimidine-2,4-(1H,3H)-dione (60 mg) and triethylamine (0.067 ml) in anhydrous dichloromethane (2 ml) at room temperature. After 1 hour, saturated sodium hydrogen carbonate solution (10 ml) was added and the mixture was extracted with ether (2×10 ml). The organic extracts were dried over anhydrous magnesium sulfate, filtered and evaporated under reduced pressure. The residue was purified by preparative normal-phase HPLC with isohexane:ethyl acetate gradient elution then recrystallised from ethyl acetate:isohexane to give the title compound (28 mg).

m.p. 216–217° C.

MS (+ve APCI) 658 ((M+H)$^+$)

$^1$H NMR (CDCl$_3$) δ0.88 (6H, d), 2.10–2.24 (1H, m), 3.29 (3H, s), 3.34 (6H, s), 3.63 (2H, d), 4.72 (2H, s), 7.15–7.18 (2H, m), 7.34–7.51 (6H, m), 7.82 (1H, d), 7.87 (1H, d), 7.95 (1H, d).

EXAMPLE 33

5-[(3-Methoxycarbonylaminophenyl)thio]-3-methyl-1-(2-methylpropyl)-6-(1-naphthalenylmethyl)thieno[2,3-d]pyrimidine-2,4-(1H,3H)-dione Methyl chloroformate (0.028 ml) was added to a solution of 5-[(3-aminophenyl)thio]-3-methyl-1-(2-methylpropyl)-6-(1-naphthalenylmethyl)thieno[2,3-d]pyrimidine-2,4-(1H,3H)-dione (60 mg) and triethylamine (0.067 ml) in anhydrous dichloromethane (2 ml) at room temperature. Further triethylamine (0.067 ml) and methyl chloroformate (0.028 ml) were added after 4 hours and 24 hours. Saturated sodium hydrogen carbonate solution (10 ml) was added and the mixture was extracted with ether (2×10 ml). The organic extracts were dried over anhydrous magnesium sulfate, filtered and evaporated under reduced pressure. The residue was purified by preparative normal-phase HPLC with dichloromethane:ethanol gradient elution and then recrystallised from ethyl acetate:isohexane to give the title compound (15 mg).

m.p. 167–168° C.

MS (+ve APCI) 560 ((M+H)$^+$)

$^1$H NMR (CDCl$_3$) δ0.89 (6H, d), 2.11–2.24 (1H, m), 3.34 (3H, s), 3.63 (2H, d), 3.74 (3H, s), 4.73 (2H, s), 6.52 (1H, s, br), 6.93 (1H, d), 7.17–7.35 (3H, m), 7.35–7.50 (4H, m), 7.80–7.91 (3H, m).

EXAMPLE 34

5-[(3-Acetamidophenyl)thio]-3-methyl-1-(2-methylpropyl)-6-(1-naphthalenylmethyl)thieno[2,3-d]pyrimidine-2,4-(1H,3H)-dione Acetic anhydride (0.034 ml) was added to a solution of 5-[(3-aminophenyl)thio]-3-methyl-1-(2-methylpropyl)-6-(1-naphthalenylmethyl)thieno[2,3-d]pyrimidine-2,4-(1H,3H)-dione (60 mg) and triethylamine (0.067 ml) in anhydrous dichloromethane (2 ml) at room temperature. After 1 hour, work-up and purification as in Example 32 gave the title compound (15 mg).

m.p. 173–174° C.

MS (+ve APCI) 544 ((M+H)$^+$)

$^1$H NMR (CDCl$_3$) δ0.88 (6H, d), 2.08–2.24 (1H, m), 2.14 (3H, s), 3.34 (3H, s), 3.63 (2H, d), 4.73 (2H, s), 6.97 (1H, d), 7.08 (1H, s, br), 7.22 (1H, t), 7.35–7.50 (6H, m), 7.81 (1H, d), 7.86 (1H, d), 7.91 (1H, d).

EXAMPLE 35

3-Methyl-1-(2-methylpropyl)-6-(1-naphthalenylmethyl)5-[(4-nitrophenyl)thio]thieno[2,3-d]pyrimidine-2,4-(1H,3H)-dione A solution of lithium diisopropylamide (2.6 mmol) in anhydrous tetrahydrofuran (7.5 ml) was added dropwise to a solution of 3-methyl-1-(2-methylpropyl)-6-(1-naphthalenylmethyl)thieno[2,3-d]pyrimidine-2,4(1H,3H)-dione (1.00 g) in anhydrous tetrahydrofuran (20 ml) at −78° C. under nitrogen. After 15 minutes, bis(4-nitrophenyl) disulfide (0.90 g) was added and the mixture was warmed to room temperature for 16 hours. Saturated sodium hydrogen carbonate solution (100 ml) was added and the mixture was extracted with ether (2×100 ml). The organic extracts were dried over anhydrous magnesium sulfate, filtered through a silica pad and evaporated under reduced pressure to give the crude product (1.4 g). A portion of this material (0.14 g) was purified by preparative normal-phase HPLC with dichloromethane:ethanol gradient elution and then recrystallised from ethyl acetate:isohexane to give the title compound (28 mg).

m.p. 184–185° C.

MS (+ve APCI) 532 ((M+H)$^+$)

$^1$H NMR (CDCl$_3$) δ0.91 (6H, d), 2.15–2.28 (1H, m), 3.32 (3H, s), 3.66 (2H, d), 4.73 (2H, s), 7.25 (2H, d), 7.33–7.51 (4H, m), 7.82–8.11 (3H, m), 8.12 (2H, d).

EXAMPLE 36

5-[(4-Aminophenyl)thio]-3-methyl-1-(2-methylpropyl)-6-(1-naphthalenylmethyl)thieno[2,3-d]pyrimidine-2,4-(1H,3H)-dione A suspension of the crude 3-methyl-1-(2-methylpropyl)-6-(1-naphthalenylmethyl)-5-[(4-nitrophenyl)thio]thieno[2,3-d]pyrimidine-2,4-(1H,3H)-dione (Example 35, 1.26 g), iron powder (0.59 g) and ammonium chloride (0.56 g) in ethanol (5 ml) and water (5 ml) was heated at reflux for 4 hours, then cooled to room temperature. Sodium hydroxide solution (10%, 50 ml) was added and the mixture was stirred for 1 hour. The resulting solution was decanted from insoluble solid. The solid and solution were in turn extracted with dichloromethane (3×50 ml) then ethyl acetate (3×50 ml). The combined organic extracts were dried over anhydrous magnesium sulfate, filtered and evaporated under reduced pressure. The residue was partially purified by column chromatography over silica, eluting with ethyl acetate:isohexane (1:1). Some pure material was recrystallised from isohexane:ethyl acetate to give the title compound (0.065 g). The remaining material was purified by preparative normal-phase HPLC with dichloromethane:ethanol gradient elution to give the title compound (0.163 g).

m.p. 177–178° C.

MS (+ve APCI) 502((M+H)$^+$)

$^1$H NMR (CDCl$_3$) δ0.86 (6H, d), 2.07–2.20 (1H, m), 3.37 (3H, s), 3.59 (2H, d), 3.68 (2H, s, br), 4.74 (2H, s), 6.61 (2H, d), 7.28 (2H, d), 7.34–7.51 (4H, m), 7.81 (1H, d), 7.87 (1H, d), 7.90 (1H, d).

EXAMPLE 37

3-Methyl-1-(2-methylpropyl)-6-(1-naphthalenylmethyl)-5-[(5-nitropyridin-2-yl)thio]thieno[2,3-d]pyrimidine-2,4-(1H,3H)-dione A solution of lithium diisopropylamide (6.2 mmol) in anhydrous tetrahydrofuran (20 ml) was added dropwise to a solution of 3-methyl-1-(2-methylpropyl)-6-(1-naphthalenylmethyl)thieno[2,3-d]pyrimidine-2,4(1H,3H)-dione (2.00 g) in anhydrous tetrahydrofuran (40 ml) at −78° C. under nitrogen. After 20 minutes, 2,2'-dithiobis(5-nitropyridine) (1.97 g) was added and the mixture was warmed to room temperature for 1 hour. Saturated sodium hydrogen carbonate solution (200 ml) was added and the mixture was extracted with ethyl acetate (200 ml). A solid suspended in the organic extracts was collected by filtration, washed with ethyl acetate and dried in vacuo at 40° C. to give the title compound (2.14 g).

m.p. 200–201° C.

MS (+ve APCI) 533 ((M+H)$^+$)

$^1$H NMR (CDCl$_3$) δ0.91 (6H, d), 2.15–2.29 (1H, m), 3.30 (3H, s), 3.66 (2H, d), 4.72 (2H, s), 7.28 (1H, d), 7.35–7.51 (4H, m), 7.81 (1H, d), 7.87 (1H, d), 7.93 (1H, d), 8.27 (1H, dd), 9.20 (1H, d).

EXAMPLE 38

2-{[1,2,3,4-Tetrahydro-3-methyl-1-(2-methylpropyl)-6-(1-naphthalenylmethyl)-2,4-dioxothieno[2,3-d]pyrimidin-5-yl]thio}pyridine N-oxide A solution of lithium diisopropylamide (1.55 mmol) in anhydrous tetrahydrofuran (5 ml) was added dropwise to a solution of 3-methyl-1-(2-methylpropyl)-6-(1-naphthalenylmethyl)thieno[2,3-d]pyrimidine-2,4(1H,3H)-dione (0.50 g)) in anhydrous tetrahydrofuran (10 ml) at −78° C. under nitrogen. After 20 minutes, 2,2'-dithiobis(pyridine N-oxide) (0.40 g) was added and the mixture was warmed to room temperature. After 2 hours, saturated sodium hydrogen carbonate solution (100 ml) was added and the mixture was extracted with ethyl acetate (3×50m). The organic extracts were dried over anhydrous magnesium sulfate, filtered and evaporated under reduced pressure. The residue was purified by column chromatography over silica, eluting with ethyl acetate:methanol (19:1) and then recrystallised from ethyl acetate to give the title compound (0.18 g).

m.p. 228–229° C.

MS (+ve APCI) 504 ((M+H)$^+$)

$^1$H NMR (DMSO d$_6$) δ0.86 (6H, d), 2.03–2.16 (1H, m), 3.15 (3H, s), 3.64 (2H, d), 4.74 (2H, s), 6.86 (1H, dd), 7.17–7.27 (2H, d), 7.34 (1H, td), 7.42–7.53 (3H, m), 7.86 (1H, dd), 7.91 (1H, d), 7.93 (1H, d), 8.36 (1H, dd).

EXAMPLE 39

5-[(3-Azidopropyl)thio]-3-methyl-1-(2-methylpropyl)-6-(1-naphthalenylmethyl)thieno[2,3-d]pyrimidine-2,4(1H,3H)-dione a) 3-[(1,2,3,4-Tetrahydro-3-methyl-1-(2-methylpropyl)-6-(1-naphthalenylmethyl) -2,4-dioxothieno[2,3-d]pyrimidin-5-yl)thio]propyl methanesulfonate 5-[(3-Hydroxypropyl)thio]-3-methyl-1-(2-methylpropyl)-6-(1-naphthalenylmethyl)thieno[2,3-d]pyrimidine-2,4(1H,3H)-dione (Example 4) (403 mg) was dissolved in dichloromethane (6 ml). Triethylamine (300 μl) was added followed by methanesulfonyl chloride (150 μl) and the mixture was stirred overnight. Sodium bicarbonate (aqueous) was added and the phases were separated. The aqueous phase was extracted twice with dichloromethane, the organic phases were combined, washed with brine, dried, filtered and evaporated to give the subtitle compound (0.57 g).

MS (+ve APCI) 547 ((M+H)$^+$)

$^1$H NMR (CDCl$_3$) δ0.89 (6H, d), 2.09 (2H, quint), 2.09–2.24 (1H, m), 3.16 (2H, t), 3.00 (3H, s), 3.42 (3H, s), 3.64 (2H, d), 4.37 (2H, t), 4.77 (2H, s), 7.34 (1H, d), 7.45 (1H, t), 7.51–7.54 (2H, m), 7.82 (1H, d), 7.87–7.90 (1H, m), 7.99–8.02 (1H, m).

b) 5-[(3-Azidopropyl)thio]-3-methyl-1-(2-methylpropyl)-6-(1-naphthalenylmethyl)thieno[2,3-d]pyrimidine-2,4(1H,3H)-dione 3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl methanesulfonate (0.57 g) and sodium azide (501 mg) were suspended in dimethyformamide (7 ml). The suspension was sonicated (cleaning bath) for 3 h. Water was added and the suspension was extracted thrice with ethyl acetate. The extracts were combined and washed successively with brine, water and brine, then dried, filtered and evaporated. Chromatography (isohexane:ethyl acetate 4:1 to 3:1) gave a yellow oil which was triturated with cyclohexane to give the title compound (118 mg).

m.p. 94–96°

MS (+ve APCI) 494 ((M+H)$^+$)

$^1$H NMR (DMSO d$_6$) δ0.81 (6H, d), 1.79 (2H, quin), 1.98–2.10 (1H, m), 3.05 (2H, t), 3.25 (3H, s), 3.46 (2H, t), 3.60 (2H, d), 4.78 (2H, s), 7.41 (1H, d), 7.50 (1H, t), 7.52–7.59 (2H, m), 7.88 (1H, d), 7.95–7.98 (1H, m), 8.06–8.09 (1H, m).

EXAMPLE 40

5-[(3-Aminopropyl)thio]-3-methyl-1-(2-methylpropyl)-6-(1-naphthalenylmethyl)thieno[2,3-d]pyrimidine-2,4(1H,3H)-dione 5-[(3-Azidopropyl)thio]-3-methyl-1-(2-methylpropyl)-6-(1-naphthalenylmethyl)thieno[2,3-d]pyrimidine-2,4(1H,3H)-dione (656 mg), 1,3-propanedithiol (100 μl) and triethylamine (400 μl) were dissolved in a mixture of dichloromethane (3 ml) and isopropanol (5 ml). Sodium borohydride (78 mg) was added and the mixture was stirred overnight. The solvents were removed by evaporation then dilute hydrochloric acid was added dropwise until effervescence ceased. The solution was made alkaline with aqueous sodium hydroxide and then extracted with dichloromethane (four times). The extracts were dried, filtered and evaporated. Purification by HPLC (ethanol:dichloromethane 5–40:95–60) followed by trituration with ether-cyclohexane gave the title compound (280 mg).

MS (+ve APCI) 468 ((M+H)$^+$)

$^1$H NMR (CDCl$_3$) δ0.88 (6H, d), 1.82 (2H, quint), 2.11–2.22 (1H, m), 2:88 (2H, t), 3.12 (2H, t), 3.42 (3H, s), 3.63 (2H, d), 4.78 (2H, s), 7.35 (1H, d), 7.45 (1H, t), 7.49–7.52 (2H, m), 7.82 (1H, d), 7.87–7.89 (1H, m) and 8.02–8.04 (1H, m).

5-[(3-Aminopropyl)thio]-3-methyl-1-(2-methylpropyl)-6-(1-naphthalenylmethyl)thieno[2,3-d]pyrimidine-2,4(1H,3H)-dione (142 mg) was dissolved in dichloromethane-ethanol and 1M HCl in ether (1 ml) was added. The solution was evaporated, then the solid was triturated with ethyl acetate to give the title compound as the hydrochloride salt monohydrate (62 mg).

m.p. 200–205° elemental: found: C, 57.42%, H 6.02%, N 7.87%, S 11.90%, theory for C$_{25}$H$_{32}$ClN$_3$O$_{22}$: C 57.51%, H 6.18%, N 8.05%, S 12.28%

MS (+ve APCI) 468 ((M+H)$^+$)

$^1$H NMR (DMSO d$_6$) δ0.82 (6H, d), 1.83 (2H, quint), 1.99–2.12 (1H, m), 2.94 (2H, t), 3.05 (2H, t), 3.26 (3H, s), 3.61 (2H, d), 4.78 (2H, s), 7.40 (1H, d), 7.50 (1H, t), 7.53–7.62 (2H, m), 7.78 (3H, br), 7.89 (1H, d), 7.96–7.99 (1H, m) and 8.06 (1H, d).

EXAMPLE 41

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}acetamide 5-[(3-Aminopropyl)thio]-3-methyl-1-(2-methylpropyl)-6-(1-naphthalenylmethyl)thieno[2,3-d]pyrimidine-2,4(1H,3H)-dione (51 mg) and triethylamine (100 μl) were dissolved in dichloromethane (2 ml) and acetyl chloride (25 μl) was added. The reaction was stirred overnight, then water was added and the phases were separated. The aqueous phase was extracted with dichloromethane, then the organic phases were combined, dried, filtered and evaporated. Purification by HPLC (ethanol:dichloromethane 1–10:99–90) gave the title compound (36 mg).

m.p. 114–117°

MS (+ve APCI) 510 ((M+H)$^+$)

$^1$H NMR (DMSO d$_6$) δ0.81 (6H, d), 1.67 (2H, quint), 1.78 (3H, s), 1.99–2.11 (1H, m), 2.99 (2H, t), 3.14 (2H, q), 3.25 (3H, s), 3.59 (2H, d), 4.77 (2H, s), 7.41 (1H, d), 7.49 (1H, t), 7.52–7.58 (2H, m), 7.84–7.89 (2H, m), 7.95–7.98 (1H, m) and 8.06–8.09 (1H, m).

EXAMPLE 42

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-N', N'-dimethylurea Prepared from 5-[(3-aminopropyl)thio]-3-methyl-1-(2-methylpropyl)-6-(1-naphthalenylmethyl)thieno[2,3-d]pyrimidine-2,4(1H,3H)-dione (10 mg) and dimethylcarbamoyl chloride (24.8 mg) following the method of Example 41 to give the title compound (8 mg).

MS (+ve APCI) 539 ((M+H)$^+$)

$^1$H NMR (CDCl$_3$) δ0.88 (6H, d), 1.89 (2H, quint), 2.10–2.24 (1H, m), 2.94 (6H, s), 3.12–3.17 (2H, m), 3.40 (3H, s), 3.51 (2H, q), 3.64 (2H, d), 4.78 (2H, s), 5.44 (1H, t), 7.35 (1H, d), 7.44 (1H, t), 7.48–7.53 (2H, m), 7.81 (1H, d), 7.87–7.90 (1H, m) and 8.02–8.05 (1H, m).

EXAMPLE 43

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-methoxyacetamide Prepared from 5-[(3-aminopropyl)thio]-3-methyl-1-(2-methylpropyl)-6-(1-naphthalenylmethyl)thieno[2,3-d]pyrimidine-2,4(1H,3H)-dione (10 mg) and methoxyacetyl chloride (53 mg) following the method of Example 41 to give the title compound (6 mg).

MS (+ve APCI) 540 ((M+H)$^+$)

$^1$H NMR (CDCl$_3$) δ0.88 (6H, d), 1.90 (2H, quint), 2.10–2.24 (1H, m), 3.07–3.14 (2H, m), 3.41 (3H, s), 3.43 (3H, s), 3.52 (2H, q), 3.63 (2H, d), 3.89 (2H, s), 4.78 (2H, s), 7.02 (1H, t), 7.35 (1H, d), 7.44 (1H, t), 7.48–7.54 (2H, m), 7.81 (1H, d), 7.87–7.90 (1H, m) and 8.00–8.04 (1H, m).

EXAMPLE 44

Methyl N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}carbamate Prepared from 5-[(3-aminopropyl)thio]-3-methyl-1-(2-methylpropyl)-6-(1-naphthalenylmethyl)thieno[2,3-d]pyrimidine-2,4(1H,3H)-dione (10 mg) and methyl chloroformate (34 mg) following the method of Example 41 to give the title compound (4 mg).

MS (+ve APCI) 526 ((M+H)$^+$)

$^1$H NMR (CDCl$_3$) δ0.88 (6H, d), 1.87 (2H, quint), 2.10–2.24 (1H, m), 3.08 (2H, t), 3.39 (2H, q), 3.43 (3H, s), 3.63 (2H, d), 3.66 (3H, s), 4.77 (2H, s), 5.51 (1H, br), 7.34 (1H, d), 7.44 (1H, t), 7.48–7.53 (2H, m), 7.82 (1H, d), 7.87–7.90 (1H, m) and 8.01–8.04 (1H, m).

EXAMPLE 45

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}methanesulfonamide 5-[(3-Aminopropyl)thio]-3-methyl-1-(2-methylpropyl)-6-(1-naphthalenylmethyl)thieno[2,3-d]pyrimidine-2,4(1H,3H)-dione (50 mg) and triethylamine (100 μl) were dissolved in dichloromethane (5 ml) and then cooled in ice. Methanesulfonyl chloride (25 μl) was added dropwise and the solution was stirred for 1 h. Aqueous ammonia (dilute) was added and the phases were separated. The aqueous phase was extracted twice with dichloromethane, the organic phases were combined, dried, filtered and evaporated. Purification by HPLC (ethyl acetate:isohexane 20–100:80–0) followed by trituration with methanol gave the title compound (43 mg).

MS (+ve APCI) 546 ((M+H)$^+$)

$^1$H NMR (DMSO d$_6$) δ0.81 (6H, d), 1.76 (2H, quint), 2.00–2.11 (1H, m), 2.87 (3H, s), 3.00–3.09 (4H, m), 3.25 (3H, s), 3.59 (2H, d), 4.77 (2H, s), 7.03 (1H, t), 7.41 (1H, d), 7.50 (1H, t), 7.52–7.60 (2H, m), 7.88 (1H, d), 7.95–7.98 (1H, m) and 8.07 (1H, d).

EXAMPLE 46

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}trifluoromethanesulfonamide 5-[(3-Aminopropyl)thio]-3-methyl-1-(2-methylpropyl)-6-(1-naphthalenylmethyl)thieno[2,3-d]pyrimidine-2,4(1H,3H)-dione (48 mg) and triethylamine (100 µl) were dissolved in dichloromethane 5 ml and then cooled to −78°. Trifluoromethanesulfonic anhydride (50 µl) in dichloromethane (2 ml) was added dropwise and the solution was stirred for 5 minutes. Ammonia in ethanol (1M, 0.5 ml) was added and the reaction mixture was allowed to warm to ambient temperature. Water was added and the phases were separated. The aqueous phase was extracted twice with dichloromethane, the organic phases were combined and dried, filtered and evaporated. Purification by HPLC (ethyl acetate:isohexane 5–40:95–60) gave the title compound (23 mg).

MS (+ve APCI) 600 ((M+H)$^+$)

$^1$H NMR (DMSO d$_6$) δ0.82 (6H, d), 1.76 (2H, quint), 2.00–2.11 (1H, m), 3.03 (2H, t), 3.25 (3H, s), 3.27 (2H, t), 3.60 (2H, d), 4.76 (2H, s), 7.39 (1H, d), 7.49 (1H, t), 7.54–7.57 (2H, m), 7.88 (1H, d), 7.96 (1H, d), 8.04 (1H, d), 9.36 (1H, s).

EXAMPLE 47

5-{[3-(1,3-dihydro-1,3-dioxo-2H-isoindol-2-yl)propyl]thio}-3-methyl-1-(2-methylpropyl)-6-(1-naphthalenylmethyl)thieno[2,3-d]pyrimidine-2,4(1H,3H)-dione 5-[(3-Hydroxypropyl)thio]-3-methyl-1-(2-methylpropyl)-6-(1-naphthalenylmethyl)thieno[2,3-d]pyrimidine-2,4(1H,3H)-dione (Example 4, 470 mg), triphenylphosphine (290 mg) and phthalimide (162 mg) were dissolved in tetrahydrofuran (7 ml). A solution of diethyl azodicarboxylate (170 µl) in tetrahydrofuran (2 ml) was added dropwise and the mixture was stirred overnight. Water and ether were added and the phases were separated. The aqueous phase was extracted with dichloromethane twice. The organic extracts were washed with brine, dried, filtered and evaporated. Column chromatography (2:1 ether:isohexane) gave a solid which was triturated hot with isohexane:ethyl acetate (4:1) and then recrystallised from isohexane:ethyl acetate (2:1) to give the title compound (12 mg).

MS (+ve APCI) 598 ((M+H)$^+$)

$_1$H NMR (DMSO d$_6$) δ0.81 (6H, d), 1.87 (2H, quint), 1.98–2.10 (1H, m), 3.01 (2H, t), 3.05 (3H, s), 3.57 (2H, d), 3.67 (2H, t), 4.77 (2H, s), 7.38 (1H, d), 7.46 (1H, t), 7.49–7.56 (2H, m), 7.82 (4H, s), 7.85 (1H, d), 7.93–7.96 (1H, m) and 8.06–8.09 (1H, m).

EXAMPLE 48

N-(2-Hydroxyethyl)-N'-[1,2,3,4-tetrahydro-3-methyl-1-(2-methylpropyl)-6-(1-naphthalenylmethyl)-2,4-dioxothieno[2,3-d]pyrimidin-5-yl)]urea Diphenylphosphoryl azide (0.27 ml) was added to a solution of 1,2,3,4-tetrahydro-3-methyl-1-(2-methylpropyl)-6-(1-naphthalenylmethyl)-2,4-dioxothieno[2,3-d]pyrimidine-5-carboxylic acid (Example 16, step a), 400 mg) and triethylamine (0.18 ml) in anhydrous toluene (12 ml). The mixture was heated at 90° C., under nitrogen for 3 hours, then cooled to room temperature to give a 0.088M solution of N-[1,2,3,4-tetrahydro-3-methyl-1-(2-methylpropyl)-6-(1-naphthalenylmethyl)-2,4-dioxothieno[2,3-d]pyrimidin-5-yl]isocyanate. Some of this solution (3 ml) was treated with ethanolamine (0.019 ml) and after 1 hour, 1M hydrochloric acid (50 ml) was added. Methanol (20 ml) was added and the mixture was extracted with ethyl acetate (5×100 ml). The combined organic extracts were washed with water (50 ml) then with saturated sodium hydrogen carbonate solution (50 ml), dried over anhydrous magnesium sulfate, filtered and concentrated under reduced pressure to a volume of about 30 ml. After 16 hours, the precipitated solid was collected by filtration and dried in vacuo to give the title compound (0.058 g).

m.p. 227–228° C.

MS (+ve APCI) 481 ((M+H)$^+$)

$^1$H NMR (DMSO d$_6$) δ0.77 (6H, d), 1.97–2.07 (1H, m), 3.19 (2H, q), 3.21 (3H, s), 3.46 (2H, q), 3.51 (2H, d), 4.43 (2H, s), 4.72 (1H, t), 7.01 (1H, t), 7.45–7.54 (4H, m), 7.86 (1H, dd), 7.92–7.95 (1H, m), 8.01–8.04 (1H, m), 8.26 (1H, s).

EXAMPLE 49

2-Hydroxyethyl[1,2,3,4-tetrahydro-3-methyl-1-(2-methylpropyl)-6-(1-naphthalenylmethyl)-2,4-dioxothieno[2,3-d]pyrimidin-5-yl]carbamate Ethylene glycol (1 ml) was added to a 0.088M solution of N-[1,2,3,4-tetrahydro-3-methyl-1-(2-methylpropyl)-6-(1-naphthalenylmethyl)-2,4-dioxothieno[2,3-d]pyrimidin-5-yl]isocyanate in toluene (Example 48, 3 ml). The mixture was heated at 90° C. for 1 hour then added to 1M hydrochloric acid (50 ml) and extracted with ether (100 ml). The organic extracts were washed with water (50 ml) and then with saturated sodium hydrogen carbonate solution (50 ml), then dried over anhydrous magnesium sulfate, filtered and evaporated under reduced pressure The residue was purified by column chromatography over silica, eluting with ether:isohexane (3:2), and then recrystallised from ethyl acetate isohexane to give the title compound (0.023 g).

m.p. 201–202° C.

MS (+ve APCI) 482 ((M+H)$^+$)

$^1$H NMR (CDCl$_3$) δ0.84 (6H, d), 2.06–1.99 (1H, m), 2.27 (1H, t), 3.38 (3H, s), 3.55 (2H, d), 3.87–3.92 (2H, m), 4.33–4.37 (2H, m), 4.57 (2H, s), 7.42–7.51 (4H, m), 7.80–7.84 (1H, m), 7.86–7.89 (1H, m), 7.93–7.97 (1H, m), 8.16 (1H, s, br).

EXAMPLE 50

N-(2-Hydroxyethyl)-N-methyl-N'-[1,2,3,4-tetrahydro-3-methyl-1-(2-methylpropyl)-6-(1-naphthalenylmethyl)-2,4-dioxothieno[2,3-d]pyrimidin-5-yl)]urea 2-(Methylamino)ethanol (0.026 ml) was added to a 0.088M solution of N-[1,2,3,4-tetrahydro-3-methyl-1-(2-methylpropyl)-6-(1-naphthalenylmethyl)-2,4-dioxothieno[2,3-d]pyrimidin-5-yl]isocyanate in toluene (Example 48, 3 ml). After 16 hours, ethyl acetate (50 ml) was added and the mixture was washed with 1M hydrochloric acid (50 ml), water (50 ml) and then saturated sodium hydrogen carbonate solution (50 ml), then dried over anhydrous magnesium sulfate, filtered and evaporated under reduced pressure. The residue was purified by column chromatography over silica, eluting with ether, then recrystallised from ethyl acetate isohexane to give the title compound (0.061 g).

m.p. 151–152° C.

MS (+ve APCI) 495 ((M+H)$^+$)

$^1$H NMR (CDCl$_3$) δ0.84 (6H, d), 2.08–2.21 (1H, m), 3.18 (3H, s), 3.23(1H, t), 3.37 (3H, s), 3.55–3.60 (4H, m), 3.87 (2H, q), 4.54 (2H, s), 7.43–7.49 (4H, m), 7.79–7.82 (1H, m), 7.85 7.88 (1H, m), 7.95–7.99 (1H, m), 8.37 (1H, s).

EXAMPLE 51

6-[(1-Hydroxy-1-(3-fluorophenyl))methyl]-3-methyl-1-(2-methylpropyl)thieno[2,3-d]pyrimidine-2,4-(1H,3H)-dione a) 6-Chloro-3-methyl-1-(2-methylpropyl)-1H-pyrimidine-2,4(1H,3H)-dione A mixture of 6-chloro-3-methyl-1H-pyrimidine-2,4(1H, 3H)-dione (J. Amer. Chem. Soc., 1980, 102, 5036) (27.85 g), 1-iodo-2-methylpropane (21.9 ml) and potassium carbonate (26.36 g) in anhydrous dimethylformamide (100 ml) was stirred at 90° C., under nitrogen for 40 hours. The reaction mixture was cooled to room temperature and diluted with water (800 ml). Brine (100 ml) was added and the mixture was extracted with ether (2×500 ml). The organic extracts were dried over anhydrous magnesium sulfate, filtered and evaporated under reduced pressure. The residual oil was triturated with ether and the resulting crystals were filtered, washed with ether and dried in vacuo to give the subtitle compound (7.38 g). The mother liquors were evaporated under reduced pressure and purified by column chromatography over silica eluting with isohexane:ether (1:1) to give further subtitle compound (6.90 g).

$^1$H NMR (CDCl$_3$) δ0.96 (6H, d), 2.10–2.24 (1H, m), 3.34 (3H, s), 3.90 (2H, d), 5.92 (1H, s).

b) 3-Methyl -1-(2-methylpropyl)-6-thioxo-pyridine-2,4(1H, 3H)-dione

To a stirred solution of 6-chloro-3-methyl-1-(2-methylpropyl)-1H-pyrimidine-2,4(1H,3H)-dione (31.5 g) in ethanol (120 ml) was added sodium hydrogen sulfide hydrate (11.83 g). After 16 hours, further sodium hydrogen sulfide hydrate (5.92 g) was added and stirring was continued for 5 hours. The reaction mixture was diluted with water and was then extracted with ethyl acetate (2×200 ml). The aqueous layer was acidified by addition of concentrated hydrochloric acid and extracted with ethyl acetate (3×500 ml). The combined organic extracts were dried over anhydrous magnesium sulfate, filtered and evaporated under reduced pressure to give the subtitle compound as a solid (25.44 g).

MS (+ve APCI) 215 ((M+H)$^+$)

$^1$H NMR (CDCl$_3$) δ0.94 (6H, d) 2.23–2.38 (1H, m), 3.32 (3H, s), 4.16 (2H, s), 4.30 (2H, d).

c) 3-Methyl-1-(2-methylpropyl)thieno[2,3-d]pyrimidin-2,4(1H,3H)-dione

Sodium acetate (38.9 g) was added to a stirred suspension of 3-methyl-1-(2-methylpropyl)-6-thioxo-pyrimidine-2,4(1H,3H)-dione (25.42 g) in water (1 l). After 5 hours, the mixture was filtered. Aqueous chloroacetaldehyde solution (50 wt. %, 142 ml) was added to the filtrate and the mixture was stirred for 16 hours. The mixture was acidified with concentrated hydrochloric acid and extracted with ethyl acetate (3×500 ml). The combined organic extracts were washed with saturated sodium hydrogen carbonate solution, dried over anhydrous magnesium sulfate, filtered and evaporated under reduced pressure. The residual oil was purified by column chromatography over silica, eluting with isohexane:ether (1:1) to give the title compound (26.78 g) as a solid.

MS (+ve APCI) 239 ((M+H)$^+$).

$^1$H NMR (CDCl$_3$) δ1.00 (6H, d), 2.26–2.42 (1H, m), 3.43 (3H, s), 3.81 (2H, d), 6.84 (1h, d), 7.36 (1H, d).

d) 6-[(1-Hydroxy-1-(3-fluorophenyl))methyl]-3-methyl-1-(2-methylpropyl)thieno[2,3-d]pyrimidine-2,4-(1H,3H)-dione To a solution of 3-methyl-1-(2-methylpropyl)thieno[2,3-d]pyrimidin-2,4(1H,3H)-dione (1) in tetrahydrofuran (20 ml) at −78° C. was added lithium diisopropylamide (1M, 6.3 ml). After 5 minutes a solution of m-fluorobenzaldehyde in tetrahydrofuran (2 ml) was added and the reaction was stirred for 2 h at −78° C. Water (10 ml) was added and the reaction was allowed to warm to room temperature, then extracted with ethyl acetate. The organic layer was separated, dried over magnesium sulfate and concentrated in vacuo. The resultant oil was chromatographed (silica), eluting with 1:1 isohexane:ethyl acetate to give the title compound (461 mg).

m.p. 54° C.

MS(+ve APCI) 363(M+H)

hu 1H NMR (DMSO d$_6$) δ0.90 (6H, d), 2.17 (1H, m), 3.22 (3H, s), 3.60–3.78 (2H, dm), 5.98 (1H, d), 6.66 (1H, d), 7.03 (1H, s), 7.11 (1H, m), 7.28 (2H, m), 7.41 (1H, m)

EXAMPLE 52

6-[(3-Fluorophenyl)methyl]-3-methyl-1-(2-methylpropyl)thieno[2,3-d]pyrimidine-2,4-(1H,3H)-dione To a solution of 6-(1-hydroxy-(3-fluorophenyl)methyl)-3-methyl-1-(2-methylpropyl)thieno[2,3-d]pyrimidine-2,4-(1H,3H)-dione (Example 51) (957 mg) in trifluoroacetic acid (7 ml) was added triethylsilane (4 ml) and the reaction was allowed to stir for 16 h. The mixture was then poured onto 10% sodium hydroxide and extracted with ethyl acetate. The organic layer was dried over magnesium sulfate and then concentrated in vacuo to a viscous oil. The oil was purified by normal phase HPLC to give the title compound (82 mg).

m.p. 76–8° C.

MS(+ve APCI) 347(M+H)

$^1$H NMR (DMSO-d$_6$) δ0.88 (6H, d), 2.16 (1H, m), 3.23 (3H, s), 3.67 (2H, d), 4.16 (2H, s), 7.04–7.18 (4H, m), 7.37 (H, m).

The following compounds were prepared from 3-methyl-1-(2-methylpropyl)thieno[2,3-d]pyrimidin-2,4(1H,3H)-dione and the appropriate aldehyde following the method of Example 51:

The following compounds were made from the corresponding alcohols (above) by the method of Example 52:

EXAMPLE 81

6-(3-Imino-1,3-dihydro-benzo[c]furan-1-yl)-3-methyl-1-(2-methylpropyl)thieno[2,3-d]pyrimidine-2,4(1H,3H)-dione To a solution of 3-methyl-1-(2-methylpropyl)thieno[2,3-d]pyrimidin-2,4(1H,3H)-dione (500 mg) in tetrahydrofuran (10 ml) at −78° C. was added lithium diisopropylamide (1M, 3.1 ml). After 5 minutes a solution of o-cyanobenzaldehyde in tetrahydrofuran (2 ml) was added and the reaction was allowed to stir for 2 h. Water (10 ml) was the added and the mixture was allowed to warm to room temperature. The mixture was extracted with ethyl acetate. The organic layer was separated and dried over magnesium sulfate, then concentrated in vacuo and purified by normal phase HPLC to yield the title compound (15 mg).

m.p. 152° C.

MS(+ve APCI) 370(M+H)

EXAMPLE 82

2-[(1,2,3,4-tetrahydro-3-methyl-1-(2-methylpropyl)-2,4-dioxothieno[2,3-d]pyrimidin-6-yl)methyl] benzamide Prepared form 6-(3-Imino-1,3-dihydro-benzo[c]furan-1-yl)-3-methyl-1-(2-methylpropyl)thieno[2,3-d]pyrimidine-2,4(1H,3H)-dione following the method of Example 52.

m.p. 183° C.

MS(+ve APCI) 372 (M+H)

$^1$H NMR DMSO-d$_6$ δ0.88(6H, d), 2.16 (1H, m), 3.32 (3H, s), 3.65 (2,H, d) 4.31 (2H, s), 7.03 (1H, s), 7.27–7.49 (5H, m), 7.88 (1H, bs).

EXAMPLE 83

(±) 6-(1-Hydroxy-1-[1-naphthalenyl]methyl)-5-([3-hydroxypropyl]thio)-3-methyl-1-(2-methylpropyl) thieno[2,3-d]pyrimidine-2,4(1H,3H)-dione a) (±) 6-(1-[Dimethyl-(1,1-dimethylethyl)silyloxy]-1-[1-naphthalenyl]methyl)-3-methyl-1-(2-methylpropyl)thieno[2,3-d]pyrimidin-2,4(1H,3H)-dione.

Dimethyl-(1,1-dimethylethyl)silyl chloride (230 mg) and imidazole (130 mg) were added to a solution of (±) 6-(1-hydroxy-1-[1-naphthalenyl]methyl)-3-methyl-1-(2-methylpropyl)thieno[2,3-d]pyrimidin-2,4(1H,3H)-dione (500 mg) in dimethylformamide (10 ml). The solution was stirred at ambient temperature for 3 days. The reaction mixture was quenched with dilute hydrochloric acid and extracted with ethyl acetate. The organic phase was separated and washed twice with dilute hydrochloric acid and once with brine, dried over magnesium sulfate and concentrated in vacuo. Purification by chromatography on silica gel eluting with isohexane:ethyl acetate (4:1 to 2:1) gave the subtitle product (0.47 g).

MS (APCI) 509 ((M+H)$^+$)

b) (±) 6-(1-Hydroxy-1-[1-naphthalenyl]methyl)-5-([3-(hydroxypropyl]thio)-3-methyl-1-(2-methylpropyl)thieno[2,3-d]pyrimidine-2,4(1H,3H)-dione.

A solution of lithium diisopropylamide (1.40 mmol) in tetrahydrofuran (5 ml) was added to a solution of (±) 6-(1-[dimethyl-1,1-dimethylethylsilyloxy]-1-[1-naphthalenyl]methyl)-3-methyl-1-(2-methylpropyl)thieno[2,3-d]pyrimidine-2,4(1H,3H)-dione (450 mg) and 3-{[dimethyl-(1,1-dimethylethyl)silyl]oxy}propyl4-methylphenylthiosulfonate (J. Med. Chem. 1995, 38, 2557., 500 mg) in tetrahydrofuran (15 ml) at −78° C. After 1 h at −78° C. the reaction mixture was allowed to warm to ambient temperature. The reaction mixture was quenched with dilute hydrochloric acid and extracted with ethyl acetate. The organic phase was separated and washed twice with dilute hydrochloric acid, twice with saturated sodium hydrogen carbonate solution and once with brine, then dried over magnesium sulfate and concentrated in vacuo. The residue was dissolved in acetonitrile (3 ml) and hydrofluoric acid (40%aqueous, 0.1 ml) was added. After 24 h the reaction mixture was quenched by the addition of saturated sodium hydrogen carbonate solution and extracted into ethyl acetate. The organic phase was separated and washed twice with saturated sodium hydrogen carbonate solution and once with brine, dried over magnesium sulfate and concentrated in vacuo. Purification by chromatography on silica gel eluting with ethyl acetate gave the title compound (0.012 g).

m.p. 100–105° C.

MS (APCI) 467 ((M+H–H$_2$O)$^+$)

$^1$H NMR (DMSO d$_6$) δ0.3 (6H, t); 1.58 (2H, quin); 2.10 (1H, m); 2.87 (1H, m); 2.95 (1H, m); 3.24 (3H, s); 3.30 (2H, dt); 3.50 (1H, dd); 3.70 (1H, dd); 4.41 (1H, t); 7.14 (1H,); 7.38 (1H,); 7.49 (1H, t); 7.55–7.65 (2H, m); 7.93 (1H, d); 8.00–8.05 (2H, m).

EXAMPLE 84

3-Methyl-1-(2methylpropyl)-6-(1-naphthalenylcarbonyl)thieno[2,3-d]pyrimidine-2,4(1H,3H)-dione 1-Naphthoyl chloride (1.25 ml) was added under nitrogen to a stirred slurry of aluminium chloride (1.1 g) in 1,2-dichloroethane (10 ml). A solution of 3-methyl-1-(2-methylpropyl)thieno[2,3-d]pyrimidin-2,4(1H,3H)-dione (2.0 g) in 1,2-dichloroethane (10 ml) was added dropwise and the resultant mixture was heated under reflux for 24 h and then allowed to cool to ambient temperature. The reaction mixture was quenched by the careful addition of water (2 ml) and was then concentrated in vacuo. The residue was dissolved in ethyl acetate and washed thrice with dilute hydrochloric acid, twice with saturated sodium hydrogen carbonate solution, and once with brine, then dried over magnesium sulfate and concentrated in vacuo. Purification by chromatography on silica gel eluting with toluene:ethyl acetate (9:1) gave the title compound (0.78 g).

m.p. ~150° C.

MS (APCI) 393 ((M+H)$^+$)

$^1$H NMR (DMSO d$_6$) δ1.00 (6H, d); 2.25 (1H, m); 3.22 (3H,s); 3.80 (2H, d); 7.47 (1H, s); 7.55–7.65 (2H, m); 7.70 (1H, t); 7.85 (1H, d); 8.05 (1H, dd); 8.10 (1H, dd); 8.20 (1H, d).

EXAMPLE 85

(±)-5-[(3-Hydroxybutyl)thio]-3-methyl-1-(2-methylpropyl)-6-(1-naphthalenylmethyl)thieno[2,3-d]pyrimidine-2,4(1H,3H)-dione A solution of dimethylsulfoxide (0.113 ml) in anhydrous dichloromethane (1 ml) was added to a solution of oxalyl chloride (0.093 ml) in anhydrous dichloromethane (5 ml) at −78° C. under nitrogen. After 5 minutes, a solution of 5-[(3-hydroxypropyl)thio]-3-methyl-1-(2-methylpropyl)-6-(1-naphthalenylmethyl)thieno[2,3-d]pyrimidine-2,4(1H,3H)-dione (0.25 g) in anhydrous dichloromethane (4 ml) was added dropwise. After 10 minutes, triethylamine (0.372 ml) was added and the mixture was warmed to room temperature. Ether (30 ml) was added and the mixture was washed with 2M hydrochloric acid (10 ml) then with saturated sodium hydrogen carbonate solution (10 ml), then dried over anhydrous magnesium sulfate, filtered and evaporated. The residue was dissolved in anhydrous tetrahydrofuran (10 ml), cooled to −78° C. under nitrogen and treated with methyl magnesium chloride (3.0M solution in tetrahydrofuran, 0.265 ml). The mixture was warmed to room temperature, then added to saturated sodium hydrogen carbonate solution (30 ml) and then extracted with ethyl acetate (2×30 ml). The organic extracts were dried over anhydrous magnesium sulfate, filtered through a small silica pad and evaporated. The residue was purified by preparative normal-phase HPLC with ethyl acetate/isohexane gradient elution followed by recrystallisation from ethyl acetate/isohexane to give the title compound (58 mg).

m.p. 162–163° C.

MS (+ve APCI) 483 ((M+H)$^+$)

$^1$H NMR (CDCl$_3$) δ0.88 (6H, d), 1.25 (3H, d), 1.76–1.82 (2H, m), 2.10–2.25 (1H, m), 3.10–3.23 (3H, m), 3.42 (3H, s), 3.57–3.75 (2H, m), 4.14–4.26 (1H, m), 4.77 (2H, ABq), 7.35 (1H, d), 7.45 (1H, t), 7.50–7.56 (2H, m), 7.82 (1H, d), 7.87–7.90 (1H, m), 8.02–8.06 (1H, m).

EXAMPLE 86

6-(3-Fluorophenyl)methyl-5-[(3-hydroxypropyl) thio]-3-methyl-1-(2-methylpropyl)thieno[2,3-d] pyrimidine-2,4(1H,3H)-dione A tetrahydrofuran solution of lithium diisopropylamide (5.0 ml, 0.72 mmol) was added to a solution of 6-(3-fluorophenyl)methyl-3-methyl-1-(2-methylpropyl)thieno[2,3-d]pyrimidine-2,4(1H,3H)-dione (Example 52, 0.24 g) in anhydrous tetrahydrofuran (5 ml), at −79° C. under nitrogen. After 15 minutes, further lithium diisopropylamide solution (2.5 ml, 0.36 mmol) was added. The reaction mixture was maintained at −78° C. for a further 3 hours. 3-{[Dimethyl-(1,1-dimethylethyl)silyl]oxy}propyl4-methylphenylthiosulfonate (J. Med. Chem. 1995, 38, 2557, 0.286 g) was added and the mixture was heated at 50° C. for 30 minutes. The reaction mixture was added to saturated sodium hydrogen carbonate solution (50 ml) and extracted with ether (50 ml). The organic extracts were dried over anhydrous magnesium sulfate, filtered and evaporated. The residue was dissolved in acetonitrile (10 ml) and then treated with 40% hydrofluoric acid (1 ml). After 1 hour, the mixture was added to saturated sodium hydrogen carbonate solution (100 ml) and extracted with ether (2×50 ml). The organic extracts were dried over anhydrous magnesium sulfate, filtered and evaporated. The residue was purified by column chromatography over silica, eluting with ethyl acetate:isohexane (1:1) followed by recrystallisation from ethyl acetate/isohexane to give the title compound (0.058 g).

m.p. 99–100° C.

MS (+ve APCI) 437 ((M+H)$^+$)

$^1$H NMR (CDCl$_3$) δ0.96 (6H, d), 1.84 (2H, quin), 2.19–2.34 (1H, m), 2.76 (1H, t), 3.06 (2H, t), 3.43 (3H, s), 3.74 (2H, d), 3.85 (2H, q), 4.32 (2H, s), 6.90–7.02 (3H, m), 7.25–7.32 (1H, m).

EXAMPLE 87

5-[(5-Amino-2-pyridinyl)thio]-3-methyl-1-(2-methylpropyl)-6-(1-naphthalenylmethyl)thieno[2,3-d]pyrimidine-2,4(1H,3H)-dione Iron powder (0.85 g) and ammonium chloride (0.81 g) were added to a stirred suspension of 3-methyl-1-(2-methylpropyl)-6-(1-naphthalenylmethyl)-5-[(5-nitropyridin-2-yl)thio]thieno[2,3-d]pyrimidine-2,4-(1H, 3H)-dione (Example 37, 2.02 g) in ethanol (10 ml) and water (10 ml). The mixture was heated at reflux for 3 hours, then cooled to room temperature. 2M Sodium hydroxide solution (50 ml) was added and the mixture was stirred vigorously for 1 hour, ethyl acetate (100 ml) was added and the two-phase mixture was filtered. The solid and aqueous layer were in turn washed with ethyl acetate (100 ml). 2M Hydrochloric acid (25 ml) was added to the solid and the mixture was stirred for 1 hour, then added to the sodium hydroxide solution and extracted with ethyl acetate (2×100 ml). The combined organic extracts were dried over anhydrous magnesium sulfate, filtered and evaporated. The residue was recrystallised from ethyl acetate to give the title compound (1.07 g). The mother liquors were evaporated and purified by column chromatography over silica, eluting with ethyl acetate, and then recrystallised from ethyl acetate to give further title compound (0.665 g).

m.p. 208–209° C.

MS (+ve APCI) 503 ((M+H)$^+$)

$^1$H NMR (DMSO d$_6$) δ0.81 (6H, d), 1.97–2.02 (1H, m), 3.15 (3H, s), 3.58 (2H, d), 7.72 (2H, s), 5.26 (2H, s, br), 6.89 (2H, ABq), 7.38 (1H, td), 7.45–7.55 (3H, m), 7.83 (1H, t), 7.85–7.90 (1H, m), 7.93 (1H, d), 8.02 (1H, d).

EXAMPLE 88

Ethyl 1,2,3,4-tetrahydro-3-methyl-1-(2-methylpropyl)-6-phenylmethyl-2,4-dioxothieno[2,3-d]pyrimidine-5-carboxylate a) Diethyl 2-amino-5-phenylmethylthiophene-3,4-dicarboxylate Prepared from sulfur (0.85 g), triethylamine (3.69 ml), ethyl 2-oxo-4-phenylbutyrate (5.00 ml) and ethyl cyanoacetate (2.81 ml) in dimethylformamide (15 ml) following the method of Example 1, step b to give the subtitle compound (4.13 g) as an oil.

MS (+ve APCI) 334 ((M+H)$^+$)

$^1$H NMR (CDCl$_3$) δ1.30 (3H, t), 1.33 (3H, t), 3.94 (2H, s), 4.24 (2H, q), 4.30 (2H, q), 5.88 (2H, s, br), 7.20–7.35 (5H, m).

b) Diethyl 2-(2-methylpropyl)amino-5-phenylmethylthiophene-3,4-dicarboxylate

Prepared from sodium borohydride (2.2 g) and diethyl 2-amino-5-phenylmethylthiophene-3,4-dicarboxylate (4.10 g) in 2-methylpropanoic acid (20 ml) following the method of Example 3 step b to give the subtitle compound (2.39 g) as an oil.

MS (+ve APCI) 390 ((M+H)$^+$)

$^1$H NMR (CDCl$_3$) δ0.94 (6H, d), 1.29 (3H, t), 1.33 (3H, t), 1.84–1.98 (1H, m), 2.95 (2H, t), 3.94 (2H, s), 4.20 (2H, q), 4.30 (2H, q), 7.19–7.35 (5H, m), 7.66 (1H, t, br).

c) Ethyl 1,2,3,4-tetrahydro-3-methyl-1-(2-methylpropyl)-6-phenylmethyl-2,4-dioxothieno[2,3-d]pyrimidine-5-carboxylate Prepared from acetyl chloride (0.60 ml), silver cyanate (1.35 g) and diethyl 2-(2-methylpropyl)amino-5-phenylmethylthiophene-3,4-dicarboxylate (2.38 g) following the method of Example 3 step c and treating the residue with sodium ethoxide (1.24 g) and iodomethane (1.14 ml) in ethanol (24 ml) following the method of Example 4 to give the title compound (1.58 g).

MS (+ve APCI) 401 ((M+H)$^+$)

$^1$H NMR (CDCl$_3$) δ0.93 (6H, d), 1.39 (3H, t), 2.17–2.30 (1H, m), 3.39 (3H, s), 3.69 (2H, d), 4.12 (2H, s), 4.44 (2H, q), 7.24–7.36 (5H, m).

EXAMPLE 89

1,2,3,4-Tetrahydro-3,N,N-trimethyl-1-(2-methylpropyl)-6-phenylmethyl-2,4-dioxothieno[2,3-d]pyrimidine-5-carboxamide a) 1,2,3,4-Tetrahydro-3-methyl-1-(2-methylpropyl)-6-phenylmethyl-2,4-dioxothieno[2,3-d]pyrimidine-5-carboxylic acid 1M Sodium hydroxide solution (7.5 ml) was added to a stirred solution of ethyl 1,2,3,4-tetrahydro-3-methyl-1-(2-methylpropyl)-6-phenylmethyl-2,4-dioxothieno[2,3-d] pyrimidine-5-carboxylate (1.50 g) in methanol (7.5 ml) and tetrahydrofuran (15 ml). After 16 hours, further 1M sodium hydroxide solution (7.5 ml) was added and the solution was stirred at 50° C. for a further 8 hours. Water (100 ml) was added and the solution was washed with ether (100 ml). The aqueous phase was acidified by addition of concentrated hydrochloric acid and then extracted with ethyl acetate (2×100 ml). Undissolved solid in the organic extracts was filtered and dried in vacuo at 50° C. to give the title compound (1.00 g).

m.p. 238° C. (dec)

MS (+ve APCI) 373 ((M+H)$^+$)

$^1$H NMR (DMSO d$_6$) δ0.87 (6H, d), 2.05–2.20 (1H, m), 3.25 (3H, s), 3.68 (2H, d), 4.25 (2H, s), 7.24–7.36 (5H, m), 13.92 (1H, s, br).

b) 1,2,3,4-Tetrahydro-3,N,N-trimethyl-1-(2-methylpropyl)-6-phenylmethyl-2,4-dioxothieno[2,3-d]pyrimidine-5-carboxamide Oxalyl chloride (0.087 ml) was added to a stirred solution of 1,2,3,4-tetrahydro-3-methyl-1-(2-methylpropyl)-6-phenylmethyl-2,4-dioxothieno[2,3-d]pyrimidine-5-carboxylic acid (0.37 g) and dimethylformamide (0.01 ml) in anhydrous dichloromethane (20 ml). After 1 hour, the solution was evaporated. The residue was dissolved in anhydrous tetrahydrofuran (7 ml) and 1 ml of this solution was added to a stirred mixture of 40% aqueous dimethylamine solution (1 ml) and saturated sodium hydrogen carbonate solution (2 ml). After 30 minutes water (10 ml) was added and the mixture was extracted with ethyl acetate (10 ml). The organic extracts were dried over anhydrous magnesium sulfate, filtered and evaporated. The residue was recrystallised from ethyl acetate/isohexane to give the title compound (0.025 g).

m.p. 144–146 C.

MS (+ve APCI) 400 ((M+H)$^+$)

$^1$H NMR (DMSO d$_6$) δ0.89 (6H, d), 2.08–2.21 (1H, m), 2.64 (3H, s), 2.97 (3H, s), 3.21 (3H, s), 3.59–3.76 (2H, m), 3.97 (2H, ABq)7.21–7.35 (5H, m).

EXAMPLE 90

6-[1-Hydroxy-(4-nitrophenyl)methyl]-3-methyl-1-(2-methylpropyl)thieno[2,3-d]pyrimidin-2,4(1H,3H)-dione Prepared from 3-methyl-1-(2-methylpropyl)thieno[2,3-d]pyrimidin-2,4(1H,3H)-dione (Example 51, step c) and 4-nitrobenzaldehyde following the method of Example 51, step d.

m.p. 156° C.

$^1$H NMR (DMSO d$_6$) δ0.89 (6H, d), 2.17 (1H, m), 3.21 (3H, s), 3.61–3.79 (2H, m), 6.14 (1H, d), 6.84 (1H, d), 7.10 (1H, s), 7.73 (2H, d), 8.24 (2H, d).

EXAMPLE 91

6-(4-Nitrophenylmethyl)-3-methyl-1-(2-methylpropyl)thieno[2,3-d]pyrimidin-2,4(1H,3H)-dione Prepared from 6-[1-Hydroxy-(4-nitrophenyl)methyl]-3-methyl-1-(2-methylpropyl)thieno[2,3-d]pyrimidin-2,4(1H,3H)-dione following the method of Example 52.

m.p. 127° C.

MS (+ve APCI) 372 ((M−H)$^−$)

$^1$H NMR (DMSO d$_6$) δ0.88 (6H, d), 2.18 (1H, m), 3.23 (3H, s), 3.67 (2H, d), 4.31 (2H, s), 7.15 (1H, s), 7.59 (2H, d), 8.20 (2H, d).

EXAMPLE 92

6-(4-Aminophenylmethyl)-3-methyl-1-(2-methylpropyl)thieno[2,3-d]pyrimidine-2,4(1H,3H)-dione To a solution of 6-(4-nitrophenylmethyl)-3-methyl-1-(2-methylpropyl)thieno[2,3-d]pyrimidin-2,4(1H,3H)-dione (275 mg) in ethanol (15 ml) and water (1 ml) was added iron powder (82 mg) and ammonium chloride (78 mg). The mixture was heated at 90° C. for 6 h. and then allowed to cool to room temperature. The reaction was filtered and then evaporated before being partitioned between ethyl acetate and water. The organic layer was collected, dried over magnesium sulfate, and then evaporated. The resultant oil was purified by normal phase HPLC (isohexane:ethyl acetate 80–0:20–100) to give the title compound (20 mg).

m.p. 104° C.

MS (+ve APCI) 344 ((M+H)$^+$) $^1$H NMR (DMSO d$_6$) δ0.87 (6H, d), 2.15 (1H, m), 3.22 (3H, s), 3.66 (2H, d), 3.91 (2H, s), 4.98 (2H, s), 6.51 (2H, d), 6.91 (1H, s), 6.94 (2H, d).

EXAMPLE 93

4-(3,4-Dimethoxyphenyl)-N-{4-[(1,2,3,4-tetrahydro-3-methyl-1-(2-methylpropyl)-2,4-dioxothieno[2,3-d]pyrimidin-6-yl)methyl]phenyl}-butanamide To a solution of N-ethyl-N'-[3-(dimethylamino)propyl] carbodiimide (37 mg), 1-hydroxybenzotriazole (26 mg) and 4-(3,4-dimethyloxyphenyl)butanoic acid (36 mg) in dichloromethane (6 ml) was added 6-(4-aminophenylmethyl)-3-methyl-1-(2-methylpropyl)thieno[2,3-d]pyrimidine-2,4-(1H,3H)-dione (45 mg) in dichloromethane (2 ml). The reaction mixture was stirred overnight and then washed with half saturated sodium hydrogen carbonate and extracted into ethyl acetate. The organic layer was dried over magnesium sulfate, evaporated and the residue was purified by normal phase HPLC (isohexane:ethyl acetate 50–0:50–100) to give the title compound (19 mg) as a foam.

MS (+ve APCI) 550 ((M+H)$^+$)

$^1$H NMR (DMSO d$_6$) δ0.87 (6H, d), 1.88 (2H, m), 2.01(1H, m), 2.29(2H, t), 2.51(2H, t), 3.32 (3H, s), 3.66 (2H, d), 3.73 (3H, s), 3.75 (3H, s), 4.06 (2H, s), 6.70 (1H. m). 6.72 (1H, m), 6.84 (1H, m), 7.03 (1H, s), 7.19 (2H, d), 7.53 (2H, d), 9.85 (1H, s).

EXAMPLE 94

3-Acetamido-N-(4-[1,2,3,4-tetrahydro-3-methyl-1-(2-methylpropyl)-2,4-dioxothieno[2,3-d]pyrimidin-6-yl)methyl]phenyl)benzamide Prepared following the method of Example 93 from 6-(4aminophenylmethyl)-3-methyl-1-(2-methylpropyl)thieno[2,3-d]pyrimidine-2,4-(1H,3H)-dione and 3-acetamidobenzoic acid.

m.p. 230° C.

MS (+ve APCI) 505 ((M+H)$^+$)

$^1$H NMR (DMSO d$_6$) δ0.88 (6H, d), 2.19 (1H, m), 3.23 (3H, s), 3.32 (3H, s), 3.67 (2H, d), 4.10 (2H, s), 7.06 (1H, s), 7.23 (2H, d), 7.43 (1H, t), 7.59 (1H, d), 7.71 (2H, d), 7.81 (1H, d), 8.06 (1H, s), 10.13 (1H, s), 10.24 (1H, s).

EXAMPLE 95

Inhibition of Human Mixed Lymphocyte Reaction (MLR)

The MLR test was performed in 96-well flat bottomed microtitre plates. Compounds were prepared as 10 mM stock solution in dimethyl sulphoxide. A 50 fold dilution of this was prepared in RPMI. Serial dilutions were prepared from this solution. 10 µl of the 50 fold diluted stock, or dilutions of it, were added to the well to give concentrations in the assay starting at 9.5 μm and going down. Into each well was placed 1.5×10⁵ cells from each of two responding donors in a final volume of 0.2 ml RPMI 1640 medium supplemented with 10% human serum, 2 mM L-glutamine and penicillin/streptomycin. The cells were incubated at 37° C. in a humidified atmosphere at 5% carbon dioxide for 120 hours. ³H-Thymidine (0.5 μCi) was added for the final 6 hours of the incubation. The level of radioactivity incorporated by the cells was then determined, which is a measure of T-cell proliferation.

The title compounds of Examples 1 to 94 were found to exhibit an $IA_{50}$ value of less than $1 \times 10^{-6}$ M in the above test.

What is claimed is:

1. A method of treating rheumatoid arthritis, Behcet's disease, Sjogren's syndrome, systematic sclerosis and seronegative spondyloarthropathies, including ankylosing spondylitis, psoriatic arthritis and Reiter's disease, in a patient in need of such treatment, said method comprising the step of administering to the patient a therapeutically effective amount of a compound of formula (I) wherein:

R is $-C(O)Ar^1$, $-C(R^4)(R^5)Ar^1$, or $Ar^2$;

$Ar^1$ is naphthyl, quinolyl, isoquinolyl, indolyl, benzofuranyl or benzothienyl, each of which can be optionally substituted by one or more substituents selected from $C_{1-4}$ alkyl, $C_{1-4}$ alkoxy, halogen or trifluoromethyl, or $Ar^1$ is phenyl optionally substituted by one or more substituents selected from $C_{1-4}$ alkyl, $C_{1-4}$ alkoxy, halogen, trifluoromethyl, amino, nitro, cyano, trifluoromethoxy, phenoxy, $-CH_2N(R^6)_2$, $-NHSO_2CF_3$, $C_{1-4}$alkylsulphonylamino, $-NHC(O)R^{6a}$, $CO_2R^7$ or $-C(O)NR^8R^{8a}$;

$R^4$ represents H or $C_{1-4}$ alkyl;

$R^5$ represents H or OH;

each $R^6$ independently represents H or $C_{1-4}$ alkyl;

$R^{6a}$ represents H, $C_{1-6}$ alkyl, aryl or ar$C_{1-4}$alkyl, wherein the aryl group or aryl moiety in the aralkyl group is phenyl or pyridyl, each of which may be optionally substituted by one or more substituents selected from $C_{1-4}$ alkyl, $C_{1-4}$ alkoxy, $C_{1-4}$ alkylcarbonylamino, halogen or trifluoromethyl;

$R^7$ represents H or $C_{1-4}$ alkyl;

$R^8$ and $R^{8a}$ each independently represent H, $C_{1-4}$ alkyl, phenyl or pyridyl;

$Ar^2$ is acenaphthenyl, indanyl, iminodihydrobenzofuranyl or fluorenyl, each of which can be optionally substituted by one or more substituents selected from OH, $C_{1-4}$ alkyl, $C_{1-4}$ alkoxy, halogen, or trifluoromethyl;

$R^1$ and $R^2$ are independently H, $C_{1-6}$ alkyl, $C_{3-6}$ alkenyl, $CH_2C_{3-5}$ cycloalkyl or $C_{3-6}$ cycloalkyl;

$R^3$ represents H, $X-R^9$ or $X-Ar^3$;

X represents $S(O)_n$, $C(O)NR^{10}$, $C(O)O$, $NH(CO)NR^{10}$, $NH(CO)O$ or $SO_2NR^{10}$;

n is 0, 1 or 2;

$R^9$ represents a methyl group optionally substituted by one or more substituents selected from CN, $CO_2H$, $C_{1-5}$ alkoxycarbonyl, 5-tetrazolyl, $SO_2NH_2$ or $C(O)NR^{11}R^{12}$, or $R^9$ represents $C_{2-6}$ alkyl or $C_{3-6}$ alkenyl, each of which may be optionally substituted by one or more substituents selected from OH, CN, $CO_2H$, $C_{1-5}$ alkoxy, $C_{1-5}$ alkoxycarbonyl, 5-tetrazolyl, azide, phthalimido, $SO_2NH_2$, $C(O)NR^{11}R^{12}$, $NR^{13}R^{14}$, NHC(O)$R^{15}$ or NHSO$_2R^{16}$ where $R^{11}$, $R^{12}$, $R^{13}$ and $R^{14}$ each independently represent H or $C_{1-4}$ alkyl, $R^{15}$ represents $C_{1-4}$ alkyl, $C_{1-4}$ alkoxy, di($C_{1-4}$alkyl)amino, or alkoxyalkylene containing up to 6 carbon atoms, and $R^{16}$ represents $C_{1-4}$ alkyl or trifluoromethyl; or, additionally, in the case where X represents $C(O)NR^{10}NH(CO)NR^{10}$ or $SO_2NR^{10}$, $R^9$ and $R^{10}$ together with the nitrogen atom to which they are attached may form a 4- to 7-membered heterocyclic ring which may be optionally substituted by one or more OH groups;

$R^{10}$ represents H, $C_{1-6}$ alkyl or is linked to $R^9$ as defined above; and $Ar^3$ is phenyl, pyridyl or pyridine N-oxide, each of which may be optionally substituted by one or more substituents selected from OH, $NO_2$, $NH_2$, $NHSO_2CF_3$, $C_{1-4}$ alkoxy, bis-$C_{1-4}$alkanesulphonylamino, $C_{1-4}$alkylcarbonylamino or $C_{1-4}$alkoxycarbonylamino; or a pharmaceutically-acceptable salt or solvate thereof.

2. A method according to claim 1, wherein $Ar^1$ is naphthyl, quinolyl or benzofuranyl, or a phenyl group optionally substituted by one or two substituents selected from $C_{1-4}$ alkyl, $C_{1-4}$ alkoxy, halogen, trifluoromethyl, nitro, amino, cyano, phenoxy or $-NHC(O)R^{6a}$.

3. A method according to claim 1, wherein $R^4$ represents H, methyl or ethyl.

4. A method according to claim 1, wherein $Ar^2$ is indanyl, iminodihydrobenzofuranyl or hydroxy-substituted indanyl.

5. A method according to claim 1, wherein $R^1$ and $R^2$ are independently H, $C_{1-4}$ alkyl, $C_{3-4}$ alkenyl or $C_{3-6}$ cycloalkyl.

6. A method according to claim 1, wherein $R^9$ represents a methyl group optionally substituted by $CO_2H$ or $C(O)NR^{11}R^{12}$, or a $C_{2-4}$ alkyl group which may be optionally substituted by one or two substituents selected from OH, $CO_2H$, $C_{1-5}$ alkoxycarbonyl, azide, phthalimido, $NR^{13}R^{14}$, $NHC(O)R^{15}$ or $NHSO_2R^{16}$; or $R^9$ and $R^{10}$ together with the nitrogen atom to which they are attached form a 5–6 membered heterocyclic ring which may be optionally substituted by an OH group.

7. A method according to claim 1, wherein $R^{10}$ represents H, methyl, or is linked to $R^9$ as defined in claim 1.

8. A method according to claim 1, wherein each of $R^{11}$, $R^{12}$, $R^{13}$ and $R^{14}$ represents hydrogen.

9. A method according to claim 1, wherein $R^{15}$ represents methyl, methoxy, dimethylamino or methoxymethylene.

10. A method according to claim 1, wherein $R^{16}$ represents methyl or trifluoromethyl.

11. A method according to claim 1, wherein $Ar^3$ is phenyl, pyridyl or pyridine N-oxide, each of which may be optionally substituted by one or two substituents selected from OH, $NO_2$, $NH_2$, methoxy, bis-methanesulphonylamino, methylcarbonylamino or methoxycarbonylamino.

12. A method according to claim 1, wherein the condition is rheumatoid arthritis.

13. A method according to claim 1, wherein the compound of formula (I) is selected from:

6-(4-Methoxyphenylmethyl)-3-methylthieno[2,3-d]pyrimidine-2,4(1H,3H)-dione, 6-(4-Methoxyphenylmethyl)-3-methyl-1-(2-methyl-2-propenyl)thieno[2,3-d]pyrimidine-2,4(1H,3H)-dione, 1-(2-Methylpropyl)-6-(1-naphthalenylmethyl)thieno[2,3-d]pyrimidine-2,4(1H,3H)-dione, 3-Methyl-1-(2-methylpropyl)-6-(1-naphthalenylmethyl)thieno[2,3-d]pyrimidine-2,4(1H,3H)-dione, 3-Methyl-1-(2-methylpropyl)-6-(1-naphthalenylmethyl)-5-[(2-pyridinyl)thio]thieno[2,3-d]pyrimidine-2,4(1H,3H)-dione, 5-[(3-Hydroxypropyl)thio]-3-methyl-1-(2-methylpropyl)-6-(1-naphthalenylmethyl)thieno(2,3-d]pyrimidine-2,4(1H, 3H)-dione, Methyl 4-[(1,2,3,4-tetrahydro-3-methyl-1-(2-methylpropyl)-6-(1-naphthalenylmethyl)-2,4-dioxothieno[2,3-d]pyrimidin-5-yl)thio]butanoate,
4-[(1,2,3,4-Tetrahydro-3-methyl-1-(2-methylpropyl)-6-(1-naphthalenylmethyl)-2,4-dioxothieno[2,3-d]pyrimidin-5-yl)thio]butanoic acid,
Methyl 4-[(1,2,3,4-tetrahydro-3-methyl-1-2-methylpropyl)-6-(1-naphthalenylmethyl)-2,4-dioxothieno[2,3-d]pyrimidin-5-yl)sulfinyl]butanoate,
Methyl 4[(1,2,3,4-tetrahydro-3-methyl-1-(2-methylpropyl)-6-(1-naphthalenylmethyl)-2,4-dioxothieno[2,3-d]pyrimidin-5-yl)sulfonyl]butanoate,
4-[(1,2,3,4-Tetrahydro-3-methyl-1-(2-methylpropyl)-6-(1-naphthalenylmethyl)-2,4-dioxothieno[2,3-d]pyrimidin-5-yl)sulfonyl]butanoic acid,
6-Benzyl-3-methyl-1-(2-methylpropyl)thieno[2,3-d]pyrimidine-2,4(1H,3H)-dione,
3-Methyl-1-(1-methylethyl)-6-(phenylmethyl)thieno[2,3-d]pyrimidine-2,4(1H,3H)-dione,
6-[(1-Hydroxy-1-phenyl)methyl]-3-methyl-1-(2-methylpropyl)thieno[2,3-d]pyrimidine-2,4(1H,3H)-dione.

14. A method according to claim 1, wherein the compound of formula (I) is selected from:

(±) 5-[(2-Hydroxypropyl)thio]-3-methyl-1-(2-methylpropyl)-6-(1-naphthalenylmethyl)thieno[2,3-d]pyrimidine-2,4(1H,3H)-dione,
1,2,3,4-Tetrahydro-N-(2-hydroxyethyl)-3-methyl-1-(2-methylpropyl)-6-(1-naphthalenylmethyl)-2,4-dioxothieno[2,3-d]pyrimidine-5-carboxamide,
(3R)-1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}pyrrolidin-3-ol,
1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}piperidin-4-ol,
(3R)-1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}piperidin-3-ol,
1,2,3,4-Tetrahydro-N-(2-hydroxyethyl)-3,N-dimethyl-1-(2-methylpropyl)-6-(1-naphthalenylmethyl)-2,4-dioxothieno[2,3-d]pyrimidine-5-carboxamide,
2-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}acetic acid,
3-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}propanoic acid,
2-{[1,2,3,4-Tetrahydro-3-methyl-1-(2-methylpropyl)-6-(1-naphthalenylmethyl)-2,4-dioxothieno[2,3-d]pyrimidin-5-yl]carboxamido}acetamide,
1-{[1,2,3,4-Tetrahydro-3-methyl-1-(2-methylpropyl)-6-(1-naphthalenylmethyl)-2,4-dioxothieno[2,3-d]pyrimidin-5-yl]carbonyl}pyrrolidine,
1,2,3,4=Tetrahydro-N-(2-hydroxyethyl)-3-methyl-1-(2-methylpropyl)-6-(1-naphthalenylmethyl)-2,4-dioxothieno[2,3-d]pyrimidine-5-sulfonamide,
5-[(3-Methoxyphenyl)thio]-3-methyl-1-(2-methylpropyl)-6-(1-naphthalenylmethyl)thieno[2,3-d]pyrimidine-2,4-(1H,3H)-dione,
5-[(3-Hydroxyphenyl)thio]-3-methyl-1-(2-methylpropyl)-6-(1-naphthalenylmethyl)thieno[2,3-d]pyrimidine-2,4-(1H,3H)-dione,
5-[(3-Hydroxyphenyl)sulfinyl]-3-methyl-1-(2-methylpropyl)-6-(1-naphthalenylmethyl)thieno[2,3-d]pyrimidine-2,4-(1H,3H)-dione.

15. A method according to claim 1, wherein the compound of formula (I) is selected from:

5-[(3-Hydroxyphenyl)sulfonyl]-3-methyl-1-(2-methylpropyl)-6-(1-naphthalenylmethyl)thieno[2,3-d]pyrimidine-2,4-(1H,3H)-dione,
3-Methyl-1-(2-methylpropyl)-6-(1-naphthalenylmethyl)-5-[(3-nitrophenyl)thio]thieno[2,3-d]pyrimidine-2,4-(1H,3H)-dione,
5-[(3-Aminophenyl)thio]-3-methyl-1-(2-methylpropyl)-6-(1-naphthalenylmethyl)thieno[2,3-d]pyrimidine-2,4-(1H,3H)-dione,
5-{[3-{(Bis-methanesulfonyl)amino}phenyl]thio}-3-methyl-1-(2-methylpropyl)-6-(1-naphthalenylmethyl)thieno[2,3-d]pyrimidine-2,4-(1H,3H)-dione,
5-[(3-Methoxycarbonylaminophenyl)thio]-3-methyl-1-(2-methylpropyl)-6-(1-naphthalenylmethyl)thieno[2,3-d]pyrimidine-2,4-(1H,3H)-dione,
5-[(3-Acetamidophenyl)thio]-3-methyl-1-(2-methylpropyl)-6-(1-naphthalenylmethyl)thieno[2,3-d]pyrimidine-2,4-(1H,3H)-dione,
3-Methyl-1-(2-methylpropyl)-6-(1-naphthalenylmethyl)-5-[(4-nitrophenyl)thio]thieno[2,3-d]pyrimidine-2,4-(1H,3H)-dione,
5-[(4-Aminophenyl)thio]-3-methyl-1-(2-methylpropyl)-6-(1-naphthalenylmethyl)thieno[2,3-d]pyrimidine-2,4-(1H,3H)-dione,
3-Methyl-1-(2-methylpropyl)-6-(1-naphthalenylmethyl)-5-[(5-nitropyridin-2-yl)thio]thieno[2,3-d]pyrimidine-2,4-(1H,3H)-dione,
2-{[1,2,3,4-Tetrahydro-3-methyl-1-(2-methylpropyl)-6-(1-naphthalenylmethyl)-2,4-dioxothieno[2,3-d]pyrimidin-5-yl]thio}pyridine N-oxide,
5-[(3-Azidopropyl)thio]-3-methyl-1-(2-methylpropyl)-6-(1-naphthalenylmethyl)thieno[2,3-d]pyrimidine-2,4(1H,3H)-dione,
5-[(3-Aminopropyl)thio]-3-methyl-1-(2-methylpropyl)-6-(1-naphthalenylmethyl)thieno[2,3-d]pyrimidine-2,4(1H,3H)-dione,
N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}acetamide,
N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-N',N'-dimethylurea.

16. A method according to claim 1, wherein the compound of formula (I) is selected from:

N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}-methoxyacetamide,
Methyl N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}carbamate,
N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}methanesulfonamide,
N-{3-[(1,2,3,4-Tetrahydro-3-methyl-1-(2-methylpropyl)-6-(1-naphthalenylmethyl)-2,4-dioxothieno[2,3-d]pyrimidin-5-yl)thio]propyl}trifluoromethanesulfonamide,
5-{[3-(1,3-Dihydro-1,3-dioxo-2H-isoindol-2-yl)propyl]thio}-3-methyl-1-(2-methylpropyl)-6-(1-naphthalenylmethyl)thieno[2,3-d]pyrimidine-2,4(1H,3H)-dione,
N-(2-Hydroxyethyl)-N'-[1,2,3,4-tetrahydro-3-methyl-1-(2-methylpropyl)-6-(1-naphthalenylmethyl)-2,4-dioxothieno[2,3-d]pyrimidin-5-yl)]urea, 2-Hydroxyethyl [1,2,3,4-tetrahydro-3-methyl-1-(2-methylpropyl)-6-(1-naphthalenylmethyl)-2,4-dioxothieno[2,3-d]pyrimidin-5-yl]carbamate, N-(2-Hydroxyethyl)-N-methyl-N'-[1,2,3,4-tetrahydro-3-methyl-1-(2-methylpropyl)-6-(1-naphthalenylmethyl)-2,4-dioxothieno[2,3-d]pyrimidin-5-yl)]urea, 6-[(1-Hydroxy-1-(3-fluorophenyl))methyl]-3-methyl-1-(2-methylpropyl)thieno[2,3-d]pyrimidine-2,4-(1H,3H)-dione, 6-[(3-Fluorophenyl)methyl]-3-methyl-1-(2-methylpropyl)thieno[2,3-d]pyrimidine-2,4-(1H,3H)-dione, 6-[(1-Hydroxy-1-(2-bromophenyl))methyl]-3-methyl-1-(2-methylpropyl)thieno[2,3-d]pyrimidine-2,4(1H,3H)-dione, 6-[(1-Hydroxy-1-(2-methylphenyl))methyl]-3-methyl-1-(2-methylpropyl)thieno[2,3-d]pyrimidine-2,4(1H,3H)-dione, 6-[(1-Hydroxy-1-(3-cyanophenyl))methyl]-3-methyl-1-(2-methylpropyl)thieno[2,3-d]pyrimidine-2,4(1H,3H)-dione, 6-[(1-Hydroxy-1-(3-trifluoromethylphenyl))methyl]-3-methyl-1-(2-methylpropyl)thieno[2,3-d]pyrimidine-2,4(1H,3H)-dione.

17. A method according to claim 1, wherein the compound of formula (I) is selected from:

6-[(1-Hydroxy-1-(3-phenyloxyphenyl))methyl]-3-methyl-1-(2-methylpropyl)thieno[2,3-d]pyrimidine-2,4(1H,3H)-dione, 6-[(1-Hydroxy-1-(1-naphthalenyl))methyl]-3-methyl-1-(2-methylpropyl)thieno[2,3-d]pyrimidine-2,4(1H,3H)-dione, 6-[(1-Hydroxy-1-(6-quinolinyl))methyl]-3-methyl-1-(2-methylpropyl)thieno[2,3-d]pyrimidine-2,4(1H,3H)-dione, 6-[(1-Hydroxy-1-(4-quinolinyl))methyl]-3-methyl-1-(2-methylpropyl)thieno[2,3-d]pyrimidine-2,4(1H,3H)-dione, (±) 6-[1-(Benzo[b]furan-2-yl)-1-hydroxymethyl]-3-methyl-1-(2-methylpropyl))thieno[2,3-d]pyrimidine-2,4(1H,3H)-dione, 6-[(1-Hydroxy-1-(2-chloro6-fluorophenyl))methyl]-3-methyl-1-(2-methylpropyl)thieno-[2,3-d]pyrimidine-2,4(1H,3H)-dione, 6-[(1-Hydroxy-1-phenyl)ethyl]-3-methyl-1-(2-methylpropyl)thieno[2,3-d]pyrimidine-2,4(1H,3H)-dione, 6-[(1-Hydroxy-1-(4-trifluoromethylphenyl))methyl]-3-methyl-1-(2-methylpropyl)thieno[2,3-d]pyrimidine-2,4(1H,3H)-dione, (±) 6-(2,3-dihydro-1-hydroxy-1H-indenyl)-3-methyl-1-(2-methylpropyl)thieno[2,3-d]pyrimidine-2,4(1H,3H)-dione, 6-[(1-Hydroxy-1-(2-quinolinyl))methyl]-3-methyl-1-(2-methylpropyl)thieno[2,3-d]-pyrimidine-2,4(1H,3H)-dione, 6-(1-Hydroxy-1-[3-quinolinyl]methyl)-3-methyl-1-(2-methylpropyl)thieno[2,3-d]-pyrimidine-2,4(1H,3H)-dione, 6-(2-bromophenylmethyl)-3-methyl-1-(2-methylpropyl)thieno[2,3-d]pyrimidine-2,4(1H,3H)-dione, 6-(2-methylphenylmethyl)-3-methyl-1-(2-methylpropyl)thieno[2,3-d]pyrimidine-2,4(1H,3H)-dione, 6-(3-cyanophenylmethyl)-3-methyl-1-(2-methylpropyl)thieno[2,3-d]pyrimidine-2,4(1H,3H)-dione.

18. A method according to claim 1, wherein the compound of formula (I) is selected from:

6-(3-trifluoromethylphenylmethyl)-3-methyl-1-(2-methylpropyl)thieno[2,3-d]pyrimidine-2,4(1H,3H)-dione, 6-(3-phenyloxyphenylmethyl)-3-methyl-1-(2-methylpropyl)thieno[2,3-d]pyrimidine-2,4(1H,3H)-dione, 3-Methyl-1-(2-methylpropyl)-6-(4-quinolinylmethyl)thieno[2,3-d]pyrimidine-2,4(1H,3H)-dione, 3-Methyl-1-(2-methylpropyl)-6-(6-quinolinylmethyl)thieno[2,3-d]pyrimidine-2,4(1H,3H)-dione, 3-Methyl-1-(2-methylpropyl)-6-(2-quinolinylmethyl)thieno[2,3-d]pyrimidine-2,4(1H,3H)-dione, trifluoroacetic acid salt, 6-(2-Benzo[b]furanylmethyl)-3-methyl-1-(2-methylpropyl)-)thieno[2,3-d]pyrimidine-2,4(1H,3H)-dione, 6-(2-Chloro-6-fluorophenylmethyl)-3-methyl-1-(2-methylpropyl)thieno[2,3-d]pyrimidine-2,4(1H,3H)-dione, 6-(1-Phenylethyl)-3-methyl-1-(2-methylpropyl)thieno[2,3-d]pyrimidine-2,4(1H,3H)-dione, 6-(4-Trifluoromethylphenylmethyl)-3-methyl-1-(2-methylpropyl)thieno[2,3-d]pyrimidine-2,4(1H,3H)-dione, (±) 6-(2,3-dihydro-1H-inden-1-yl)-3-methyl-1-(2-methylpropyl)thieno[2,3-d]pyrimidine-2,4(1H,3H)-dione, 6-(3-Imino-1,3-dihydro-benzo[c]furan-1-yl)-3-methyl-1-(2-methylpropyl)thieno[2,3-d]pyrimidine-2,4(1H,3H)-dione, 2-[(1,2,3,4-tetrahydro-3-methyl-1-(2-methylpropyl)-2,4-dioxothieno[2,3-d]pyrimidin-6-yl)methyl]benzamide, (±) 6-(1-Hydroxy-1-[1-naphthalenyl]methyl)-5-([3-hydroxypropyl]thio)-3-methyl-1-(2-methylpropyl)thieno[2,3-d]pyrimidine-2,4(1H,3H)-dione.

19. A method according to claim 1, wherein the compound of formula (I) is selected from:

3-Methyl-1-(2-methylpropyl)-6-(1-naphthalenylcarbonyl)thieno[2,3-d]pyrimidine-2,4(1H,3H)-dione, (±)-5-[(3-Hydroxybutyl)thio]-3-methyl-1-(2-methylpropyl)-6-(1-naphthalenylmethyl)thieno[2,3-d]pyrimidine-2,4(1H,3H)-dione, 6-(3-Fluorophenyl)methyl-5-[(3-hydroxypropyl)thio]-3-methyl-1-(2-methylpropyl)thieno[2,3-d]pyrimidine-2,4(1H,3H)-dione, 5-[(5-Amino-2-pyridinyl)thio]-3-methyl-1-(2-methylpropyl)-6-(1-naphthalenylmethyl)thieno[2,3-d]pyrimidine-2,4(1H,3H)-dione, Ethyl 1,2,3,4-tetrahydro-3-methyl-1-(2-methylpropyl)-6-phenylmethyl-2,4-dioxothieno[2,3-d]pyrimidine-5-carboxylate, 1,2,3,4-Tetrahydro-3,N,N-trimethyl-1-(2-methylpropyl)-6-phenylmethyl-2,4-dioxothieno[2,3-d]pyrimidine-5-carboxamide, 6-[1-Hydroxy-(4-nitrophenyl)methyl]-3-methyl-1-(2-methylpropyl)thieno[2,3-d]pyrimidin-2,4(1H,3H)-dione, 6-(4-Nitrophenylmethyl)-3-methyl-1-(2-methylpropyl)thieno[2,3]pyrimidin-2,4(1H,3H)-dione, 6-(4-Aminophenylmethyl)-3-methyl-1-(2-methylpropyl)thieno[2,3-d]pyrimidine-2,4-(1H,3H)-dione, 4-(3,4-Dimethoxyphenyl)-N-{4-[(1,2,3,4-tetrahydro-3-methyl-1-(2-methylpropyl)-2,4-dioxothieno[2,3-d]pyrimidin-6-yl)methyl]phenyl}-butanamide, and 3-Acetamido-N-(4-[1,2,3,4-tetrahydro-3-methyl-1-(2-methylpropyl)-2,4-dioxothieno[2,3-d]pyrimidin-6-yl)methyl]phenyl)benzamide.

* * * * *